(12) United States Patent
Susztak et al.

(10) Patent No.: US 8,377,886 B2
(45) Date of Patent: Feb. 19, 2013

(54) USE OF GAMMA SECRETASE INHIBITORS AND NOTCH PATHWAY INHIBITORS FOR TREATMENT AND PREVENTION OF RENAL DISEASE

(75) Inventors: Katalin Susztak, Cresskill, NJ (US); Bernhard Bielesz, Rye, NY (US); Thiruvur G. Niranjan, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 78 days.

(21) Appl. No.: 12/733,339

(22) PCT Filed: Sep. 4, 2008

(86) PCT No.: PCT/US2008/010362
§ 371 (c)(1),
(2), (4) Date: Apr. 30, 2010

(87) PCT Pub. No.: WO2009/035522
PCT Pub. Date: Mar. 19, 2009

(65) Prior Publication Data
US 2010/0222283 A1    Sep. 2, 2010

Related U.S. Application Data

(60) Provisional application No. 60/993,865, filed on Sep. 14, 2007.

(51) Int. Cl.
*A61K 38/05*    (2006.01)
*A61K 31/55*    (2006.01)
*A61K 31/225*    (2006.01)
*A61P 13/12*    (2006.01)

(52) U.S. Cl. ...... 514/19; 514/217; 514/548; 514/212.04

(58) Field of Classification Search .................. None
See application file for complete search history.

(56) References Cited

U.S. PATENT DOCUMENTS

| | | |
|---|---|---|
| 6,756,511 B2 | 6/2004 | Pineiro et al. |
| 6,890,956 B2 | 5/2005 | Churcher et al. |
| 6,984,626 B2 | 1/2006 | Nadin et al. |
| 7,049,296 B2 | 5/2006 | Pineiro et al. |
| 7,101,895 B2 | 9/2006 | Churcher et al. |
| 7,138,400 B2 | 11/2006 | Collins et al. |
| 7,144,910 B2 | 12/2006 | Madin et al. |
| 7,183,303 B2 | 2/2007 | Pineiro et al. |
| 2003/0166894 A1* | 9/2003 | Kapeller-Libermann et al. .......... 536/23.1 |
| 2006/0264380 A1* | 11/2006 | Hellstrom et al. .............. 514/19 |
| 2007/0066568 A1 | 3/2007 | Dalton et al. |

FOREIGN PATENT DOCUMENTS

WO    WO2004/073630    *   9/2004

OTHER PUBLICATIONS

"Glomerulonephritis" (in www.intelihealth.com/IH/ihtIH?t=31198& p=~br, IHW|~st,24479|~r, WSIH W000|~b,*|#prevent).*
Van es et al. in Nature 435(16), pp. 959-963 (2005).*
Masuda et al. in American Journal of Pathology, 159(2) (2001).*
Yum et al. in Human Pathology 15(10), 921-927 (1984).*
PCT International Preliminary Report on Patentability (dated Mar. 16, 2010) in connection with PCT International Patent Application No. PCT/US2003/010362, 6 pages.
Cheng H T et al., entitled Notch2, but not Notch1, is required for proximal fate acquisition in the mammalian nephron, Development 134, 801-811 (2007).
Cheng H T et al., entitled "The role of Notch signaling in specification of podocyte and proximal tubules within the developing mouse kidney," Kidney Int., Nov. 2005;68(5): 1951-2, Abstract Only.
Cheng H T et al., entitled "γ-Secretase activity is dispensable for mesenchyme-to-epithelium transition but required for podocyte and proximal tubule formation in developing mouse kidney," Development 130, 2003, 5031-5042.
Niranjan T et al., entitled "The Notch pathway in podocytes plays a role in the development of glomerular disease," Nature Medicine, vol. 14, No. 3, Mar. 2008, 290-298, with attached supplemental figures and tables, 13 pages.
Kretzler M et al., entitled "Notch inhibition reverses kidney failure," Nature Medicine, vol. 14, No. 3, Mar. 2008, 246-247.
Konishi J et al., entitled "Gamma-Secretase Inhibitor Prevents Notch3 Activation and Reduces Proliferation in Human Lung Cancers," Cancer Res 2007;67:(17), pp. 8051-8057.
PCT Notification of Transmittal of The International Search Report and The Written Opinion of The International Searching Authority, or the Declaration dated Nov. 28, 2008 by the U.S. Patent Office in connection with PCT International Patent Application No. PCT/US2008/10362, 8 pages.

* cited by examiner

*Primary Examiner* — Dennis Heyer
(74) *Attorney, Agent, or Firm* — Amster, Rothstein & Ebestein

(57) ABSTRACT

Methods are provided for treating and preventing renal disease in a subject by administering a gamma secretase inhibitor or a Notch pathway inhibitor to the subject.

10 Claims, 12 Drawing Sheets

USE OF GAMMA SECRETASE INHIBITORS AND NOTCH PATHWAY INHIBITORS FOR TREATMENT AND PREVENTION OF RENAL DISEASE

CROSS-REFERENCE TO RELATED APPLICATIONS

This application is a national stage entry under 35 U.S.C. §371 of PCT International Patent Application No. PCT/US2008/010362, filed Sep. 4, 2008, and claims priority to U.S. Provisional Patent Application No. 60/993,865, filed Sep. 14, 2007, the contents of which are incorporated herein by reference in their entirety into the subject application.

STATEMENT OF GOVERNMENT SUPPORT

This invention was made with government support under grant number RO1-DK076077 awarded by the National Institutes of Health (NIDDK), U.S. Department of Health and Human Services. The government has certain rights in the invention.

FIELD OF THE INVENTION

The present invention relates to treatment and prevention of kidney disease using Notch pathway inhibitors such as, for example, gamma secretase inhibitors.

BACKGROUND OF THE INVENTION

Various publications are referred to throughout this application. Citations for these references may be found at the end of the specification immediately preceding the claims. The disclosures of these publications are hereby incorporated by reference in their entireties into the subject application to more fully describe the art to which the subject application pertains.

Kidney diseases are estimated to affect up to 10 million people worldwide. Diabetic nephropathy (DNP) and focal segmental glomerulosclerosis (FSGS) are the two major causes of end-stage renal disease (ESRD), accounting for more than half of the ESRD cases in the US[1]. Diagnoses of FSGS and DNP are based on the clinical findings of proteinuria and histological scarring of the renal glomerulus, the major filtering apparatus of the kidney.

Podocytes, the visceral epithelial cells of the glomerulus, have recently taken center stage in research on the pathogenesis of FSGS. Genetic studies in both human and mouse reveal that the development of FSGS is initiated by podocyte dysfunction[2]. Inherited mutations is likely responsible for this disease in only a minor fraction of patients.

Diabetic nephropathy is characterized by mesangial expansion and thickening of the glomerular basement membrane leading to mesangial expansion and focal and nodular sclerosis of the glomerulus. Podocyte dysfunction has also repeatedly been reported in DNP[7]. The degree of albuminuria and the rate of progression correlates best with glomerular podocyte density in patients with diabetic nephropathy[8]. The mechanism of podocyte loss/dysfunction in DNP is under intense investigation; both cell detachment and apoptosis have been described as potential mechanisms[9,10]. These events might even be linked as dead cells usually detach from the GBM and cells that detach usually die. As podocytes are terminally differentiated cells and unable to replicate, both of these mechanism can lead to decreased cell density. However, it has not been known whether protection from podocyte loss or dysfunction would influence glomerular disease development.

The Notch signaling pathway comprises a family of transmembrane receptors, their ligands, negative and positive modifiers, and transcription factors[11,12]. To date, 4 mammalian receptors (Notch1 through Notch4) and at least 5 ligands (Delta 1, 3, and 4 and Jagged 1, 2) have been identified. Binding of the ligand renders the Notch receptor susceptible to metalloprotease- and γ-secretase-mediated proteolytic cleavage, which in turn results in the release of the Notch intracellular domain (ICN) from the plasma membrane and its subsequent translocation into the nucleus. Once there, ICN associates with DNA-binding protein recombination signal-binding protein Jκ/CBF1/Su (H)/Lag-1 (Rbpj) and mastermind-like (MAML) protein, which recruit additional factors with histone acetylase activity, such as p300 and p300/CREB-binding protein-associated factor. These proteins form a heteromeric complex that mediate transcription of target genes, including basic helix-loop-helix transcription factors of the hairy and enhancer of split (Hes) family and the Hes-related repressor protein (Hey) family[13].

The Notch pathway plays a crucial role in podocyte development. Genetic deletion of presenilin, Notch2 or treatment of developing kidney explants with a γ-secretase inhibitor (GSI) leads to metanephric mesenchyme that produces nephrons without glomeruli, proximal tubules, and loops of Henle but contain distal tubules that are correctly fused to the collecting duct[14-16]. This may be due to the fact that cells in the absence of active Notch2 fail to proliferate and fail to downregulate Pax2[14]. Patients with Alagille syndrome, who lack one copy of Notch2 present with similar renal developmental abnormalities as well[17]. Very little is known about Notch signaling in the kidney beyond renal development. While during development the kidney has one of the highest levels of Notch activity, very little Notch activity can be detected in the mature mouse kidney[18].

Renal disease is currently treated using angiotensin inhibitors (ACE inhibitors) and angiotensin receptor blockers, although these treatments typically only slow progression of the disease. Accordingly, there is a need for new therapy to prevent and treat renal disease.

SUMMARY OF THE INVENTION

The present invention provides methods of treating and preventing renal disease in a subject, where the methods involve administering to the subject a Notch pathway inhibitor, such as a gamma secretase inhibitor, in an amount effective to treat or prevent renal disease in the subject.

DETAILED DESCRIPTION OF THE INVENTION

Figures 1A, 1B, 1C, 1D, 1E:
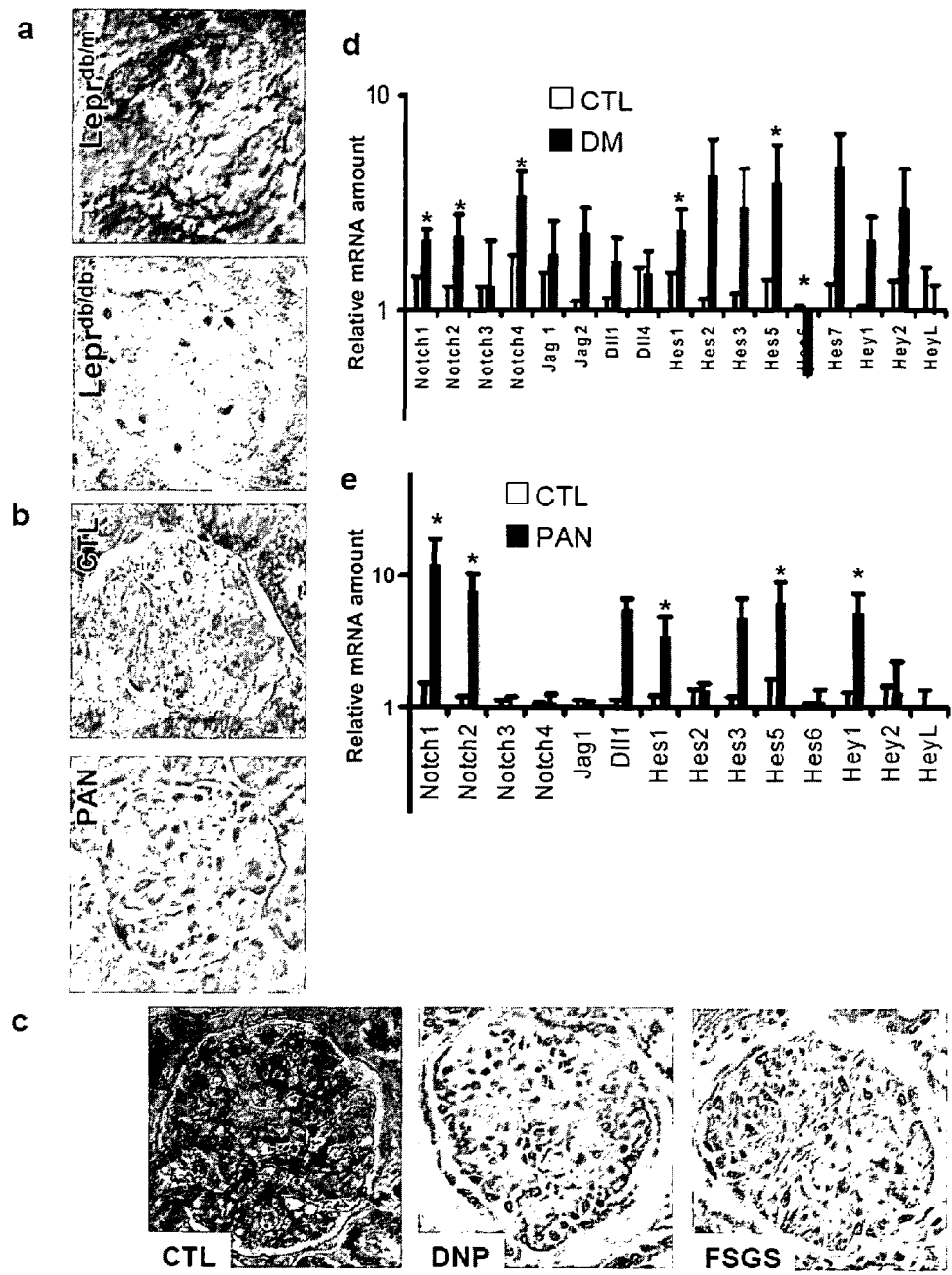
FIG. 1A-1E. Re-expression of the Notch pathway in human and animal models of glomerular disease. A. Immunostaining with Val$^{1744}$ICN1 antibody of Lepr$^{db/m}$ (control) and 8 weeks old male Lepr$^{db/db}$ (diabetic) mice and B. control (CTL) and PAN treated rats and C. human control (CTL) diabetic nephropathy (DNP) and focal segmental glomerulosclerosis (FSGS) samples, shows increased expression of active Notch1 in diseased podocytes (n=6-9/groups). d.QRT-PCR analysis shows increased relative mRNA amount of Notch pathway genes in isolated glomeruli of D. control (CTL) and streptozotocin treated diabetic mice (DM) E. and control (CTL) and PAN (PAN) treated rats. Glomerular extracts were isolated individually from each animal. * denotes p<0.01, diseased animals compared to control animals.

The present invention provides a method for treating renal disease in a subject, the method comprising administering to the subject a gamma secretase inhibitor in an amount effective to treat renal disease. The invention also provides a method of preventing renal disease in a subject, the method comprising administering to the subject a gamma secretase inhibitor in an amount effective to prevent renal disease.

The present invention provides a method for treating renal disease in a subject, the method comprising administering to the subject a Notch pathway inhibitor in an amount effective to treat renal disease. The invention also provides a method of preventing renal disease in a subject, the method comprising administering to the subject a Notch pathway inhibitor in an amount effective to prevent renal disease.

As used herein, the Notch signaling pathway comprises a family of transmembrane receptors, their ligands, negative and positive modifiers, and transcription factors[11,12]. To date, 4 mammalian receptors (Notch1 through Notch4) and at least 5 ligands (Delta 1, 3, and 4 and Jagged 1, 2) have been identified. Binding of the ligand renders the Notch receptor susceptible to metalloprotease- and γ-secretase-mediated proteolytic cleavage, which in turn results in the release of the Notch intracellular domain (ICN) from the plasma membrane and its subsequent translocation into the nucleus. Once there, ICN associates with DNA-binding protein recombination signal-binding protein Jκ/CBF1/Su (H)/Lag-1 (Rbpj) and mastermind-like (MAML) protein, which recruit additional factors with histone acetylase activity, such as p300 and p300/CREB-binding protein-associated factor. These proteins form a heteromeric complex that mediate transcription of target genes, including basic helix-loop-helix transcription factors of the hairy and enhancer of split (Hes) family and the Hes-related repressor protein (Herp, also known as Hrt/Hey) family[13]. Notch pathway inhibitors include, but are not limited to, gamma secretase inhibitors.

Renal disease can be prevented, for example, by administering a Notch pathway inhibitor or a gamma secretase inhibitor to a patient at risk for developing renal disease. Patients at risk for developing renal disease include for example subjects with diabetes.

The renal disease can be acute renal disease or chronic renal disease. Acute renal disease is characterized by sudden and rapid deterioration of kidney function. The renal disease can be progressive renal disease, in which there is a progressive loss of renal function leading to end stage kidney failure. Patients with end stage kidney failure require either renal dialysis or renal transplantation. The renal disease can involve the glomerulus and/or tubules of the kidney. Glomerular renal disease can be caused by diabetes.

Numerous gamma secretase inhibitors have been described. See, for example, U.S. Pat. Nos. 6,756,511,[42] 6,890,956,[43] 6,984,626,[44] 7,049,296,[45] 7,101,895,[46] 7,138,400,[47] 7,144,910,[48] 7,183,303;[49] Bihel et al. 2004,[50] Best et al. 2006,[51] Davies et al. 2007,[52] El-Gendy and Adejare 2004,[53] Laras et al. 2005,[54] McLendon et al. 2000,[55] Prasad et al. 2007,[56] Shearman et al. 2000,[57] and Tomita et al. 2004.[58] The following gamma secretase inhibitors are available, for example, from Calbiochem (La Jolla, Calif.):

gamma secretase inhibitor I, (GSI I), Z-Leu-Leu-Norleucine-CHO;

gamma secretase inhibitor II, (GSI

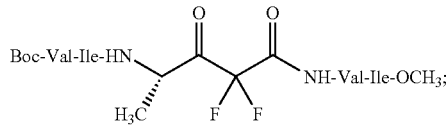

gamma secretase inhibitor III, (GSI III), N-Benzyloxycarbonyl-Leu-leucinal;

gamma secretase inhibitor IV, (GSI IV), N-(2-Naphthoyl)-Val-phenylalaninal;

gamma secretase inhibitor V, (GSI V), N-Benzyloxycarbonyl-Leu-phenylalaninal;

gamma secretase inhibitor VI, (GSI VI), 1-(S)-endo-N-(1,3,3)-Trimethylbicyclo[2.2.1]hept-2-yl)-4-fluorophenyl Sulfonamide;

gamma secretase inhibitor VII, (GSI VII), Menthyloxycarbonyl-LL-CHO;

gamma secretase inhibitor IX, (GSI IX), (DAPT), N—[N-(3,5-Difluorophenacetyl-L-alanyl)]-S-phenylglycine t-Butyl Ester;

gamma secretase inhibitor X, (GSI X), {1S-Benzyl-4R-[1-(1S-carbamoyl-2-phenethylcarbamoyl)-1S-3-methylbutylcarbamoyl]-2R-hydroxy-5-phenylpentyl}carbamic Acid tert-butyl Ester;

gamma secretase inhibitor XI, (GSI XI), 7-Amino-4-chloro-3-methoxyisocoumarin;

gamma secretase inhibitor XII, (GSI XII), Z-Ile-Leu-CHO;

gamma secretase inhibitor XIII, (GSI XIII), Z-Tyr-Ile-Leu-CHO;

gamma secretase inhibitor XIV, (GSI XIV), Z-Cys(t-Bu)-Ile-Leu-CHO;

gamma secretase inhibitor XVI, (GSI XVI), N-[N-3,5-Difluorophenacetyl]-L-alanyl-S-phenylglycine Methyl Ester;

gamma secretase inhibitor XVII, (GSI XVII), WPE-III-31C,

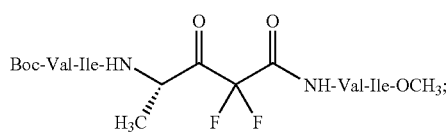

gamma secretase inhibitor XIX, (GSI XIX), (2S,3R)-3-(3,4-Difluorophenyl)-2-(4-fluorophenyl)-4-hydroxy-N-((3S)-2-oxo-5-phenyl-2,3-dihydro-1H-benzo[e][1,4]diazepin-3-yl)-butyramide;

gamma secretase inhibitor XX, (GSI XX), (Dibenzazepine (DBZ)), (S,S)-2-[2-(3,5-Difluorophenyl)acetylamino]-N-(5-methyl-6-oxo-6,7-dihydro-5H-dibenzo[b,d]azepin-7-yl)propionamide,

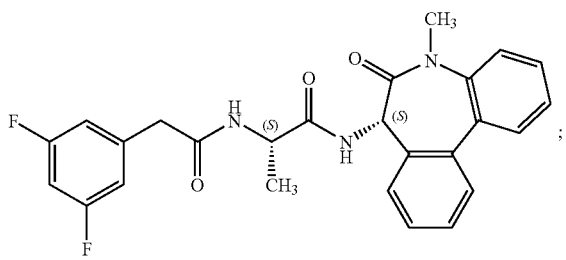

gamma secretase inhibitor XXI, (GSI XXI), (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide;

gamma40 secretase inhibitor I, N-trans-3,5-Dimethoxycinnamoyl-Ile-leucinal;

gamma40 secretase inhibitor II, N-tert-Butyloxycarbonyl-Gly-Val-Valinal; and

Isovaleryl-V-V-Sta-A-Sta-OCH$_3$.

Preferred gamma secretase inhibitors include one or more of gamma secretase inhibitor IX, N—[N-(3,5-Difluorophenacetyl-L-alanyl)]-S-phenylglycine t-Butyl Ester; gamma secretase inhibitor X, {1S-Benzyl-4R-[1-(1S-carbamoyl-2-phenethylcarbamoyl)-1S-3-methylbutylcarbamoyl]-2R-hydroxy-5-phenylpentyl}carbamic Acid tent-butyl Ester; and gamma secretase inhibitor XX dibenzazepine (DBZ), where dibenzazepine (DBZ) is most preferred.

The gamma secretase inhibitor can be administered systemically, for example, by intraperitoneal injection, intramuscular injection, subcutaenous injection or intravenous injection in a dose effective to prevent or treat renal disease in a patient.

As examples of the use of gamma secretase inhibitors, the gamma secretase inhibitor MK-0752 (Merck) has been administered to human subjects in single doses of 110 to 1000 mg (Rosen et al. 2006[59]). MK-0752 is in Phase I clinical trials for patients with breast cancer tumors (ClinicalTrials.gov Identifier NCT00106145). The gamma secretase inhibitor LY450139 (Eli Lilly) has been administered to human subjects at doses ranging from 5 mg/day to 50 mg/day for 14 days (Seimers et al. 2005[60]). A longer term study with LY450139 has been conducted at a dose of 60 mg/day for 2 weeks, followed by 100 mg/day for 6 weeks, followed by either 100 mg/day or 140 mg/day for another 6 weeks.[61]

Notch pathway inhibition can involve intervention at the level of DNA, RNA, and/or protein. For example, the presence or activity of Notch can be reduced by administration of an antisense molecule, a ribozyme, or an RNA interference (RNAi) molecule, where the antisense molecule, ribozyme or RNAi molecule specifically inhibits expression of Notch. The antisense molecule, ribozyme, or RNAi molecule can be comprised of nucleic acid (e.g., DNA or RNA) or nucleic acid mimetics (e.g., phosphorothionate mimetics) as are known in the art. Methods for treating tissue with these compositions are also known in the art. The antisense molecule, ribozyme or RNAi molecule can be administered in a pharmaceutical composition that preferably comprises an excipient that enhances penetration of the antisense molecule, ribozyme or RNAi molecule into kidney cells. The antisense molecule, ribozyme or RNAi can be expressed from a vector that is transfected into the kidney. The presence or activity of the Notch can be reduced, for example, by administration of an antibody or aptamer, wherein the antibody or aptamer specifically binds to and reduces the activity of Notch. The antibody or aptamer can be administered directly, preferably in a pharmaceutical composition comprising an agent that enhances penetration of the antibody or aptamer into kidney cells. The antibody or aptamer can be encoded on a vector that is used to transfect kidney tissue. Notch pathway inhibitors also include metalloprotease inhibitors.

The invention provides for the use of a gamma secretase inhibitor or a Notch pathway inhibitor for treating and/or preventing renal disease, and for the use of a gamma secretase inhibitor or a Notch pathway inhibitor for the preparation of a medicament for treating and/or preventing renal disease.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Example 1

Glomerular Disease

Overview

Genes in the Notch pathway were shown to be re-expressed in podocytes in humans and animal models of DNP and FSGS. The expression of ICN1 in podocytes leads apoptosis, in vivo and in vitro and the development of albuminuria and glomerulosclerosis in vivo. Conversely, genetic deletion of Notch transcriptional binding partner (Rbpj) selectively in podocytes or pharmacological inhibition of Notch cleavage (by a γ-secretase inhibitor administration) prevents from podocyte apoptosis and the development of albuminuria. The results indicate that reactivation of the Notch pathway in podocytes plays an important role in the development of glomerular disease and represents a novel pharmacological target. The role of Notch in tubular disease is addressed in Example II.

Materials and Methods

Reagents. DBZ was purchased from Calbiochem and later custom synthesized by Syncom (Groningen, Netherlands). Recombinant (carrier free) VEGF and TGFβ were purchased from R&D Biosystems.

Human kidney samples. Samples were collected from archived kidney biopsies and from nephrectomies at the AECOM Dept of Pathology. All cases are obtained from biopsy proven DNP and FSGS with significant proteinuria. The study was approved by the Institutional Board Review.

Animals. Podocyte specific conditional ICN1 overexpressing mice. Transgenic mice carrying the tet-O-Notch1IC. and podocin rtTA transgenes have previously been described[23, 24]. Four individual founder lines were crossed, and wild type or double or single transgenic animals were identified at 3 weeks of age by genomic PCR analysis using transgene specific primers. Animals were placed on doxycycline containing chow starting at 4 weeks of age.

To generate mice with Rbpj deletion specifically in podocytes, Rbpj$^{flox/flox}$ mice[40] were crossed with podocin cre mice[30]. Male littermates of the podocin$^{cre}$/Rbpj$^{flox/flox}$× pod$^{cre}$Rbpj$^{WT/flox}$ matings were used for the study. Uninephrectomies were performed on 4 weeks old male mice, under sterile conditions. To induce diabetes in mice, 10 male C57/B6J mice were injected with streptozotocin protocol (50 mg/kg ip. daily×5, low dose protocol) as detailed by the Animal Models of Diabetic Complications Consortium (AM-DCC) (www.amdcc.org). Mice were sacrificed at 20 weeks of age.

Male Sprague Dawley rats (75-100 gr~4 weeks old) were purchased from Charles Rivers. Animals were injected with puromycin aminonucleoside 20 mg/kg ip ×1. BDZ (dissolved in Methocell, Tween-80) was administered ip 500 µg/100 gr rat once a day. Animals were sacrificed on day 8 after PAN administration.

Adriamycin-induced nephrotic syndrome was induced in 8 weeks old male Balb/c mice (n=10/per each groups) via intravenous injection (to the tail vein) of 12 mg/kg adriamycin. Animals were sacrificed 12 days following the injection. All animal studies were approved by the Animal Care Committee at the Albert Einstein College of Medicine (AECOM). Animals were maintained under specific pathogen free conditions.

Phenotypic analysis. Albuminuria was determined using Mouse or Rat Albumin specific ELISA kits (Exocell and Bethyl Laboratories) and urine creatinine was determined using Creatinine companion (Exocell), following manufacturer's protocol.

Histologic analysis. Histologic analysis was performed on formalin fixed paraffin embedded kidney sections that was stained with Periodic-Acid-Schiff (PAS) or Gomori Trichrome. Slides were examined and pictures were taken with Nikon Eclipse TE300 microscope and SPOT Diagnostic CCD camera. Transmission electron microscopy was performed in the Analytical Imaging Facility at AECOM on glutaraldehyde fixed, epoxy embedded kidney samples stained with uranyl acetate and lead citrate. Samples were evaluated using JEOL 1200EX, electron microscope (AECOM, Analytical Imaging Facility).

Immunohistochemistry. Immunohistochemistry was performed on formalin fixed paraffin embedded kidney sections using the following primary antibodies Val$^{1744}$ICN1 (Abcam), ICN2 (Abeam). Staining was visualized using peroxidase conjugated anti mouse of anti rabbit Vectastain Elite kit and DAB (Vector Labs). Terminal d-UTP labeling (TUNEL) staining was performed using TUNEL kit (Chemicon) following manufacturer's instructions. For fluorescent labeling, 5 µm frozen sections were fixed in ice cold acetone, blocked with 10% horse serum and incubated with primary antibodies, WT-1 (Santa Cruz), nephrin (kind gift of Dr Lawrence Holzman, University of Michigan), synaptopodin and podocin (Sigma-Aldrich), p21 (Santa Cruz), and developed using FITC conjugated anti-mouse secondary antibody or Cy3 conjugated anti-rabbit antibodies (Jackson laboratory) and mounted with Fluoromount).

Glomerular isolation. Glomerular isolation was performed using serial sieving of 120, 100 and 71 µm diameter.

QRT-PCR. RNA was prepared from isolated glomeruli or from podocytes using RNAeasy Mini kit (Qiagen, Valencia). The quality was analyzed on agarose gels and the quantity was measured on NanoDrop. 1 ug RNA was reverse transcribed using cDNA Archival Kit (Applied Biosystems). QRT-PCR analysis was performed using ABI 7900HT-Sequence Detection System. SYBR Green Master Mix and 3-step standard cycling conditions and sequence specific primers for QRT-PCR analysis were used. Melting curve was examined to verify that a single product was amplified. For quantitative analysis all samples were normalized to ubiquitin C and HPGRT gene expression using the ΔΔCT value method.

Infection of Podocytes. Cultivation of conditionally immortalized mouse podocytes was performed as described[41]. Briefly, cells were propagated in the undifferentiated state on type1 collagen at 33° C. in RPMI 1640 in the presence of 10% FBS (Hyclone) and 20 U/ml interferon γ (Sigma Chemical Co., St Louis, Mo.). To induce differentiation, cells were maintained at 37° C. without interferon for 10 days. Podocytes were infected with MIGR-ICN1-EGFP (kind gift of Dr Warren Pear, University of Pennsylvania) or pBMN-EGFP (Orbigen) retrovirus. Briefly vectors were transfected into Phoenix Eco packaging cells (Orbigen) and supernatant was harvested 60-72 hrs after transfection. Podocytes were infected with virus containing supernatant (3-4 times, every 6 hours) in the presence of polybrene 4 mg/ml. After 24 hrs of infection, the medium was changed and cells were either treated with tamoxifen to induce ICN1 expression or left untreated. Infection efficiency was estimated under fluorescence microscope by the presence of GFP positive cells as it ranged from 70-80%.

Western Blotting. Cells were lysed in RIPA buffer in the presence of protease and phosphatase inhibitors; equal amount (30 µg) of protein was loaded on 10% SDS gels. Gels were transferred to PVDF membranes (Bio-Rad), blocked in 5% milk and incubated with the primary antibody (1:1,000 dilution) overnight at 4° C. in 1% milk. Membranes were incubated with HRP conjugated anti-mouse or anti-rabbit secondary antibody (Jackson Immunologicals) for 1 hr at room temperature and developed using ECL method (Pierce). The following primary antibodies were used in this study; phospho-p38 (#4631), total p38 (#9217), phospho-AKT (#4051), total AKT (#9272), cleaved PARP, cleaved caspase3, phospho-53 were from Cell Signaling, phospho-JNK, p53, p21 were from Santa Cruz Val$^{1744}$ICN1 and β-actin antibody was purchased from Abcam (Cambridge, Mass.).

AnnexinV staining. AnnexinV staining was performed using AnnexinV-Alexa 568 staining kit (Roche). Cells were cultured in 24 well plates, washed and incubated with AnnexinV-Alexa 568 in incubation buffer according to manufacturer's instruction. Cells were washed, and fluorescent labeled cells were counted. Total number of cells were counted by DAPI counterstain. Nuclear condensation was assessed by DAPI staining.

Statistical Analysis. Results are presented as mean standard error. Student t-test was used to analyze the difference between two groups. The Bonferroni correction was used, when more than two groups were present. Values were regarded significant at P<0.05.

Results

Reactivation of Notch Pathway in Glomerulosclerosis

Figures 2A, 2B, 2C:
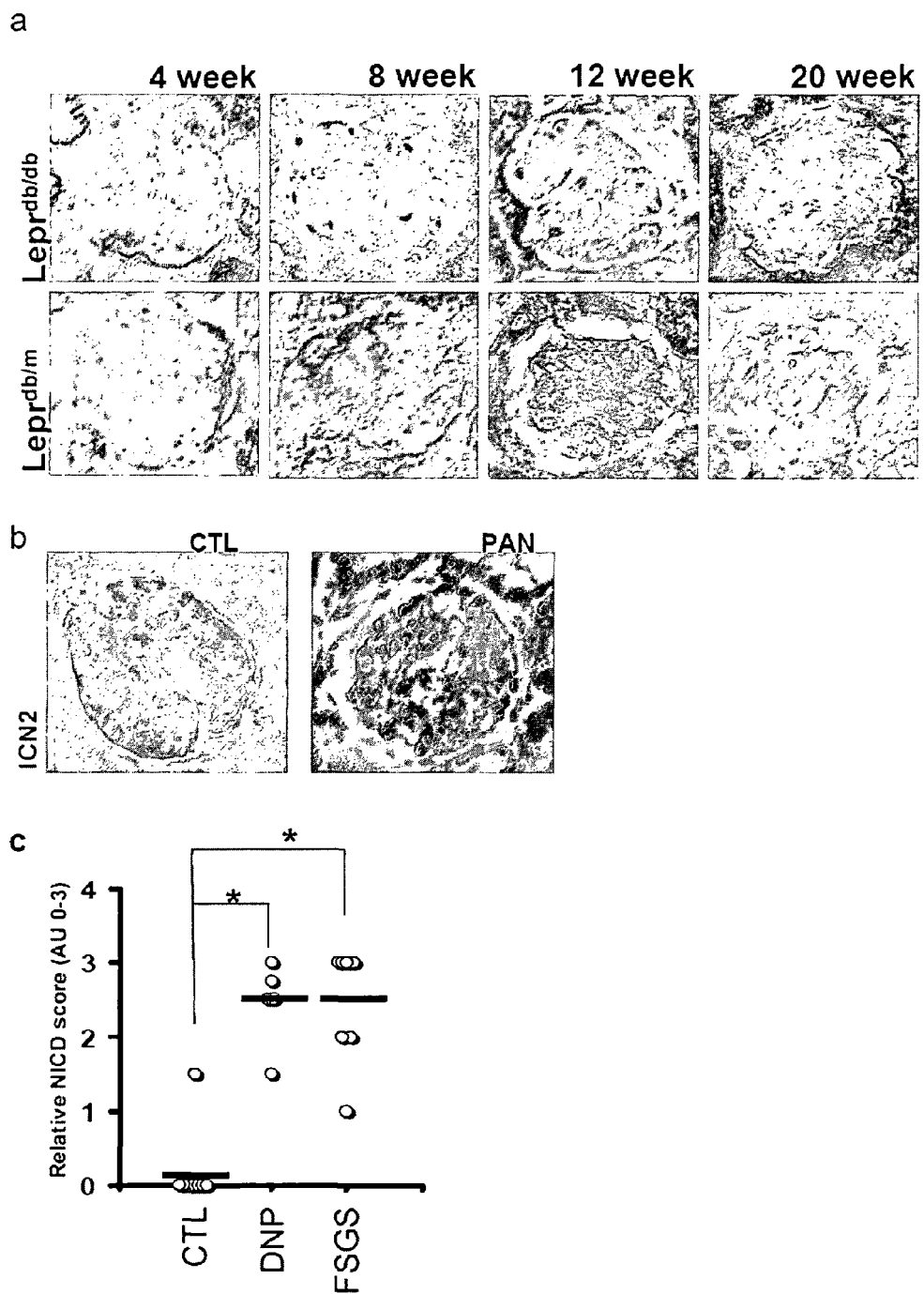
FIG. 2A-2C. Re-expression of the Notch pathway in human and animal models of glomerular disease A. Immunostaining with Val$^{1744}$ICN1 antibody of Lepr$^{db/m}$ (control) and 4, 8, 12, 20 weeks old male Lepr$^{db/db}$ (diabetic) mice. B. Immunostaining with Hes-1 antibody control (CTL) and PAN treated rats. C. Semiquantitative assessment (on arbitrary units of 1-4) of the ICN1 immunostaining in human control (CTL) diabetic nephropathy (DNP) and focal segmental glomerulosclerosis (FSGS) samples (n=6-9/per each groups). Each point represent the score of an individual biopsy, the line represent the group average. * denotes p<0.01

Active Notch1 expression was not observed in the glomerulus of healthy animals in the mature kidney, consistent with prior reports[18, 21, 22]. Type2 diabetic Lepr$^{db/db}$ mice had increased val$^{1744}$ICN1 staining at 8 weeks of age (at the time of development of hyperglycemia and the peak of podocyte injury) when compared to non-diabetic Lepr$^{db/m}$ littermates (FIG. 1a, FIG. 2a). Similarly in puromycin aminonucleotide (PAN) treated rats (a model of albuminuria and FSGS) increased val$^{1744}$ICN1 and Hes-1 staining was observed compared to untreated controls (FIG. 1b, FIG. 2c). The staining pattern in both cases was suggestive for glomerular epithelial specific staining.

Kidney biopsy samples were tested from control non-diseased kidneys and from patients with biopsy documented DNP and FSGS (n=6-9). Val$^{1744}$ICN1 staining was increased in glomeruli of human DNP and FSGS samples (FIG. 1c). The staining pattern was again consistent with glomerular epithelial labeling (FIG. 1c). Semi-quantitative assessment of the staining is shown on FIG. 2b.

In order to quantitatively assess the expression of the Notch pathway genes, QRT-PCR analysis was performed on glomerular samples obtained from control and streptozotocin diabetic mice (n=10/group) and control and PAN (puromycin aminonucleotide) induced albuminuric rats (n=10/group). mRNA levels of Notch1, Notch2, and their target gene levels Hes1, 5 and Hey1 were increased in diseased glomeruli compared to control animals (FIGS. 1d, 1e), indicating that the Notch pathway is (re)activated in human and experimental models of diabetic nephropathy and focal segmental glomerulosclerosis.

Podocyte Specific Active Notch1 Expression Leads to Massive Proteinuria and Glomerulosclerosis In order to understand whether Notch1 reactivation could play a role in the development of glomerular disease in a proof of concept experiment, active ICN1 was conditionally expressed in mature podocytes. This was achieved by breeding the podocyte specific transactivator rtTA (NPHS2/rtTA) mice[23] with the Tet-O—ICN1 mice[24] carrying the Notch1 intracellular domain after a tetracycline responsive elements (FIG. 4a)[23, 24]. Mice were born at the expected Mendelian frequency and appeared healthy. To induce the transactivator expression, mice were placed on doxycycline containing food starting at 4 weeks of age (after kidney development is complete). Immunostaining with $^{val1744}$ICN1 antibody (FIG. 4c) and QRT-PCR analysis for Notch pathway genes in glomeruli isolated from wild type, single or double transgenic animals after 10 days of doxycycline (dox) containing diet (FIG. 4b) verified the successful transgene expression.

Figures 3A, 3B, 3C, 3D, 3E, 3F:
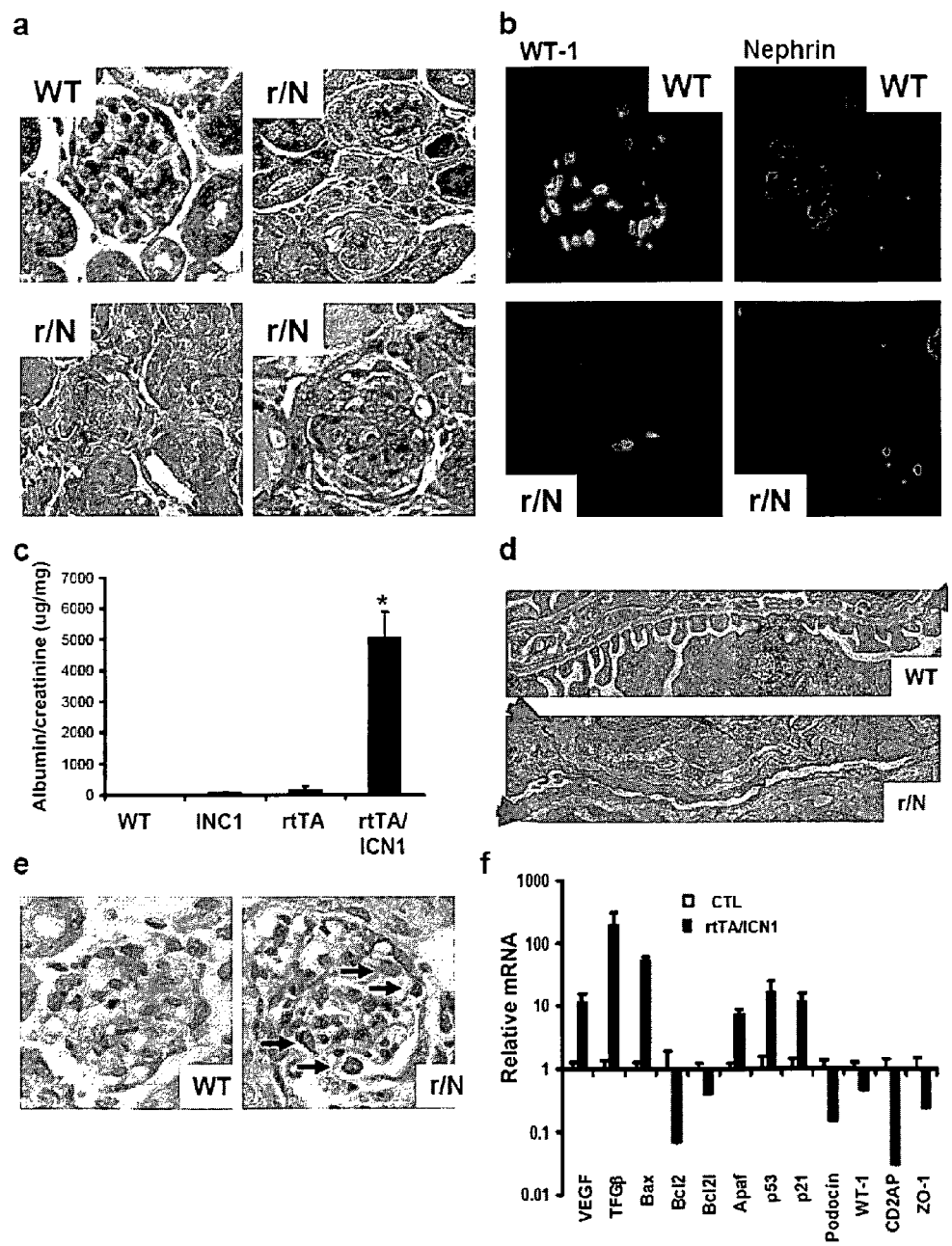
FIG. 3A-3F. Conditional de novo ICN1 expression in vivo in podocytes leads to albuminuria and severe glomerulosclerosis. A. Trichrome staining and B. WT-1 and nephrin immunostaining of kidney section of wild type (WT) and podrtTA/tet-O—ICN1 transgenic (r/N) animals on day 10 following doxycycline treatment. Single transgenic animals showed similar pattern to wild type mice. C. Albumin creatinine ratios on day 10 of doxycycline treatment of wild type (WT), podocin rtTA(rtTA), tet-O—ICN1 (ICN1) and podrtTA/tet-O—ICN1 (rtTA/ICN1) transgenic animals. D. Transmission EM analysis showed severe foot process effacement of wild type and double transgenic animals. Arrows show the glomerular basement membrane. Original magnification, ×4,000. E. Positive TUNEL staining in podocytes of double transgenic animals, compared to wild type mice. Arrows indicate positive TUNEL staining of nuclei of double transgenic animals. F. QRT-PCR analysis of glomerular gene expression in isolated glomeruli of single or double transgenic animals fed with doxycycline for 10 days. Control (CTL) represents wild type and single transgenic animals, while rtTA/ICN1 represents the expression in double transgenic animals. Glomerular extracts were isolated individually from each animal. *represents p<0.05 double transgenic animals compared to control animals FIG. 4A-4D. A. Generation of mice with inducible ICN1 expression in glomerular podocyte via intercrossing of podocin rtTA and tet-O—ICN1 mice. Doxycycline administration induces the transgene expression in double transgenic mice. B. QRT-PCR analysis of ICN1 and Hes1,5 and Hey-2 expression in glomeruli of single or double transgenic animals fed with doxycycline for 10 days. C. Val$^{1744}$ICN1 staining in kidneys of tet-O—ICN1xpodocinrtTA (r/N) and wild type (WT) mice treated with doxycycline. D. Survival analysis of CTL (wild type and single transgenic) and double transgenic animals placed on dox diet at 4 weeks of age. Animals develop albuminuria 3-5 days following initiation of dox diet.
Figures 4A, 4B, 4C, 4D:
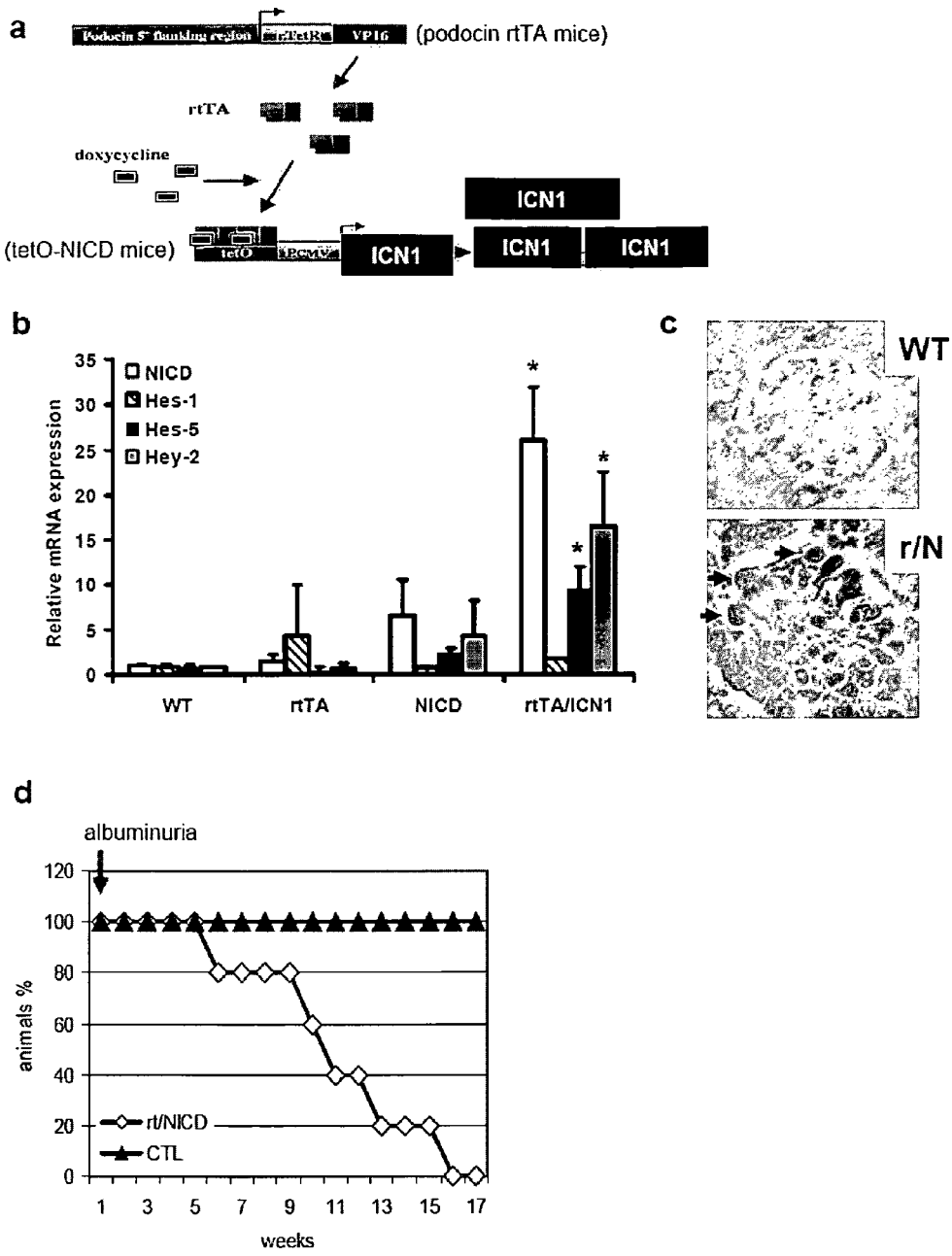

Double transgenic animals developed high grade proteinuria within 4-5 days following placement on dox diet. At 10 days after the initiation of the dox diet, double transgenic animals developed massive proteinuria, around 5,000 μg/mg albumin/creatinine in their urine while wild type or single transgenic mice had approximately 100 μg albumin/mg creatinine in their urine (FIG. 3c). Histologic examination of the dox treated double transgenic animals showed severe glomerulosclerosis (FIG. 3a). Tubules appeared dilated with proteinaceous precipitations (FIG. 3a). Double transgenic animals died (likely due to renal failure) at 6-15 weeks after the initiation of dox diet (FIG. 4d). QRT-PCR analysis performed on isolated glomeruli from double transgenic animals showed that transforming growth factor beta (TGFβ) and vascular endothelial growth factor (VEGF) mRNA levels were 10-100-fold increased compared to wild type and single transgenic animals. Podocyte specific transcript levels (podocin, CD2AP, WT-1) showed severe reduction (FIG. 3f). No significant differences were observed in Pax-2 and vimentin levels, genes that are expressed in "dedifferentiated" podocytes (data not shown). Immunohistochemistry also showed severe reduction (almost absence) of WT-1 and nephrin immunostaining in the glomerulus (FIG. 3b). Transmission electron microscopy (TEM) analysis confirmed the reduction in podocyte number and severe foot process effacement and stress in the remaining podocytes evident as villous transformation and vacuolization (FIG. 3d). TUNEL staining showed increased podocyte apoptosis in ICN1 (double transgenic) kidneys compared to controls (FIG. 3e). Glomerular epithelial cells were PCNA negative by immunostaining, confirming the absence of proliferation (data not shown). In conjunction QRT-PCR analysis of isolated glomerular samples showed increased in p53, p21, Bax and Apaf mRNA levels and a decrease in anti-apoptotic bcl-2 and bcl-21 level (FIG. 3f), indicating podocyte apoptosis.

In summary, conditional reactivation of Notch1 specifically in podocytes led to severe podocyte dysfunction, effacement, apoptosis, albuminuria, severe glomerulosclerosis and end stage kidney failure.

Active Notch1 Expression in Podocytes Leads to Apoptosis

Figures 5A, 5B, 5C, 5D, 5E:
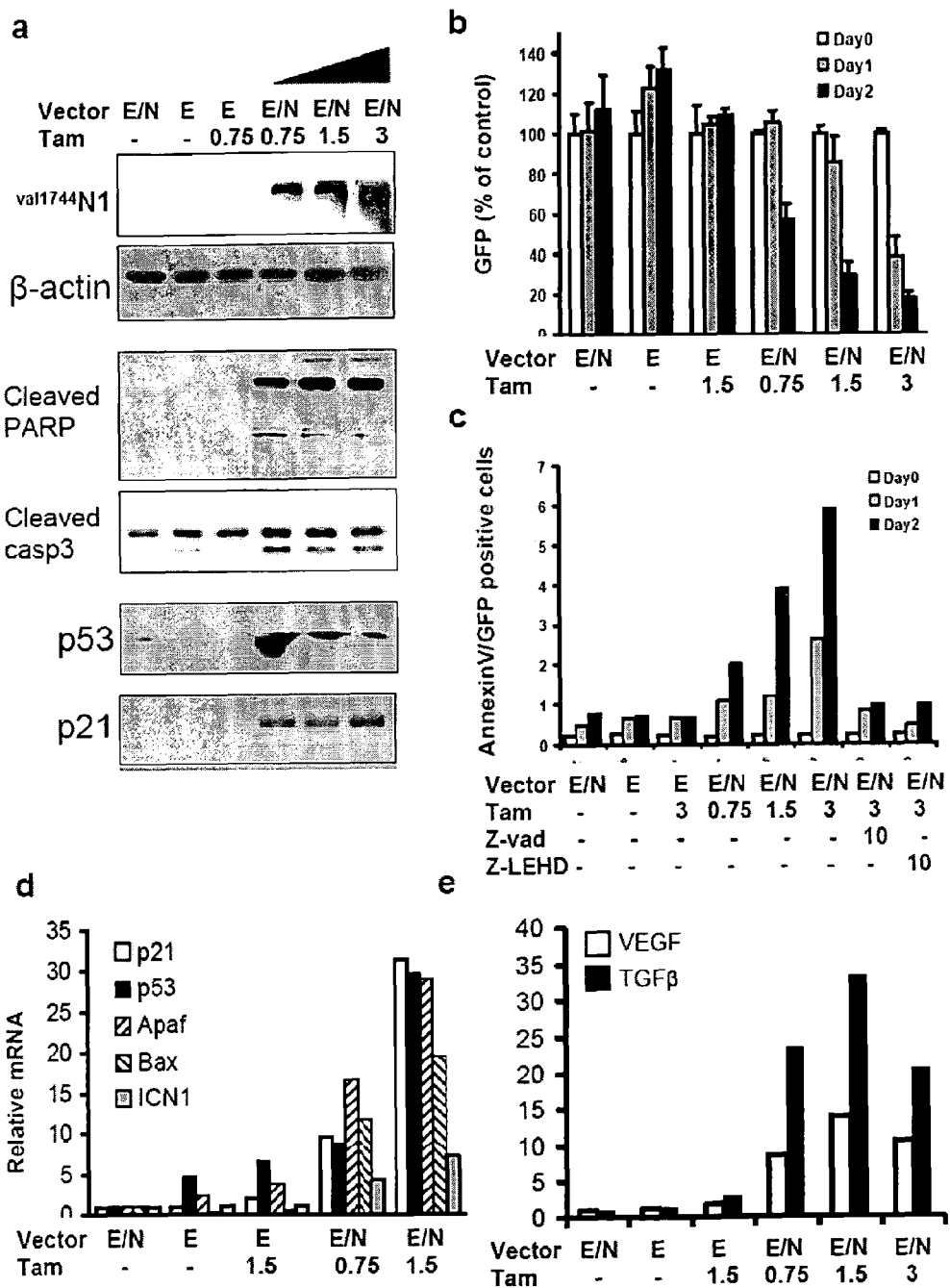
FIG. 5A-5E. ICN1 expression in podocytes leads to apoptosis Podocytes infected with MIGR/ICN1/EGFP (E/N) or BMZ/EGFP (E) retrovirus and treated with sham or tamoxifen (tam) (0.75-3 µM) A. Western Blot analysis of Val$^{1744}$ICN1, β-actin, cleaved PARP, cleaved caspase3, p53 and p21 levels 48 hrs after treatment with tamoxifen or sham. B. GFP positive cells of 0, 1 and 2 days following tamoxifen treatment (same infection scheme). 100% represents the number of GFP positive cells on day 0 (which is 24 hrs after the infection). C. The ratio of AnnexinV/GFP positive cells of infected podocytes 0, 1 and 2 days following sham or tamoxifen treatment. Cells when indicated were also treated with Z-vad (10 µM) or Z-LEHD (10 µM) at the time of the treatment with tamoxifen. D. Relative mRNA amount of p53, p21, Apaf, Bax and ICN1 of control and ICN1 overexpressing podocytes. e. Cells were treated with sham or tamoxifen (1.5 µM) to induce ICN1 expression in the presence of GSIXX (4 µM) or pifithrin-alpha (PF) (15 µM). The percent of annexinV positive cells were counted 24 hrs after the induction with tamoxifen. The data is a representative of 3-4 independent experiments.
Figures 6A, 6B, 6C:
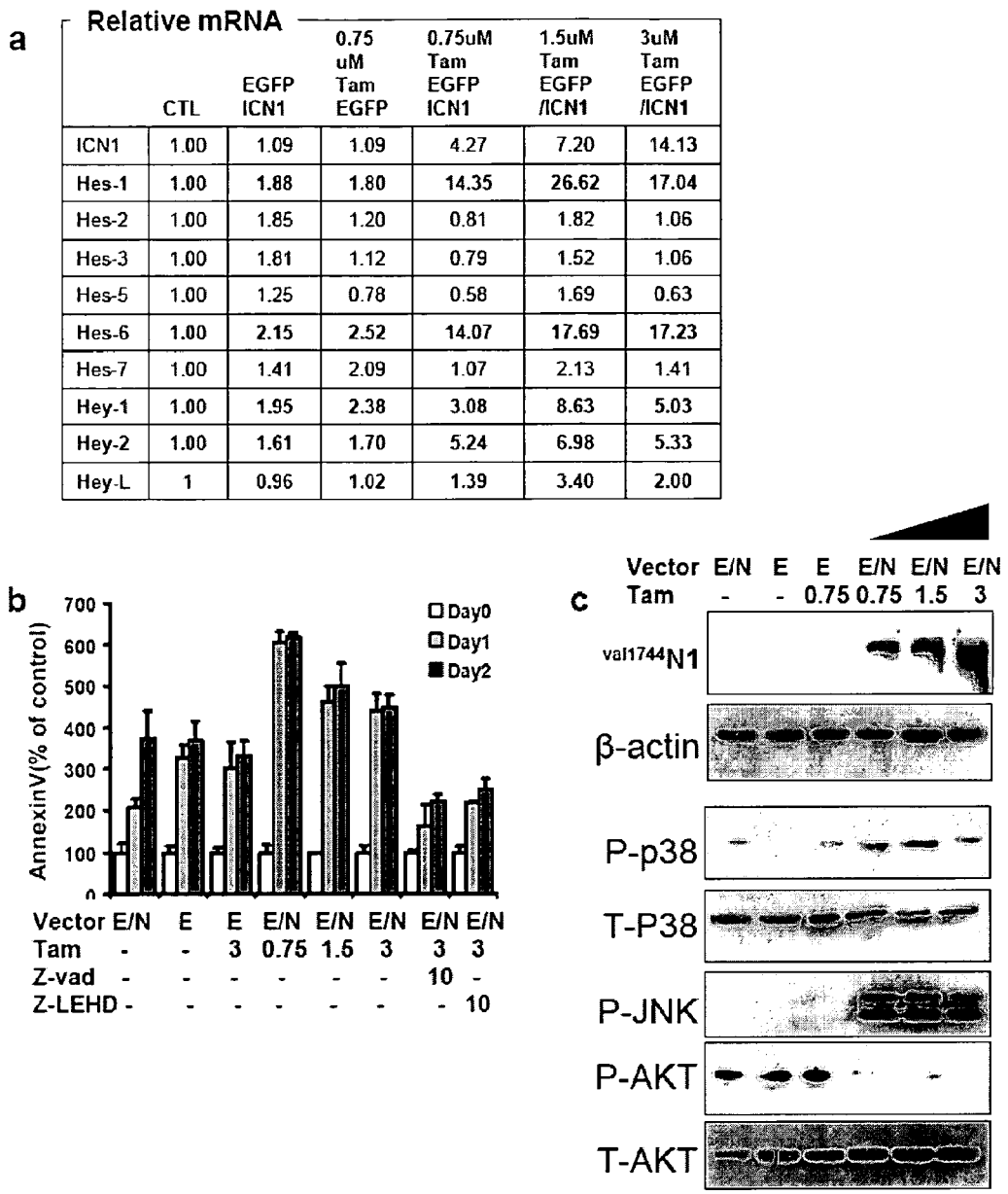
FIG. 6A-6C. Podocytes infected with MIGR/ICN1/EGFP (E/N) or BMZ/EGFP (E) retrovirus and treated with sham or tamoxifen (0.75-1.5, 3 µM). A. QRT-PCR analysis of ICN1, Hes-1,2,3,5,6,7,Hey1,2, L, VEGF and TGFβ levels. B. Percent of AnnexinV positive cells positive cells of infected podocytes 0, 1 and 2 days following sham or tamoxifen treatment. Cells when indicated were also treated with Z-vad or Z-LEHD at the time of the treatment with tamoxifen. Tamoxifen, Z-vad and Z-LEHD concentrations are shown in µM. C. Western analysis of ICN1, beta actin, phospho-p38, phospho-AKT and total p38, and AKT levels following ICN1 overexpression. The data is a representative of 3-4 independent experiments.

To further understand the role of Notch1 in podocytes, murine podocytes were transduced cultured with retroviral constructs expressing either a human ICN1 and EGFP or EGFP only, from the vector control (MigR1) under a tamoxifen regulated promoter[25]. ICN1 was not detectable in control or vector transfected murine podocytes (FIG. 5a). Treatment of MigICN1 transduced cells with tamoxifen lead to a dose dependent increase in ICN1 mRNA (FIG. 5d), protein (FIG. 5a) and target genes Hes1, Hes6, Hey1, 2 and L mRNA levels (FIG. 6a). Induction of ICN1 expression (with tamoxifen) caused a dramatic (up to 80%) dose and time dependent decline in GFP$^+$ cell number (FIG. 5b). This indicates that ICN1 expression leads to growth arrest, cell death or detachment. To differentiate between these possibilities, AnnexinV staining was performed, which is an early apoptosis marker. AnnexinV positive cell number was significantly increased as early as 24 hrs after the induction (FIG. 6b). The percent of AnnexinV/GFP positive cell number showed a dose and time dependent increase following tamoxifen treatment, indicating apoptosis (FIG. 5c, FIG. 6b). Pretreatment of the cells with Z-vad or Z-LEHD a pan-caspase and caspase-9 inhibitor, respectively prevented the ICN1 induced apoptosis, indicating the role of caspases (FIG. 5c). Western blots showed increased cleaved caspase3 and cleaved PARP levels in ICN1 expressing podocytes, confirming apoptosis (FIG. 5a).

Q-PCR analysis showed that p53, p21, Bax and Apaf levels were significantly increased in ICN1 overexpressing cells (FIG. 5d). Western Blotting confirmed the increase in p53 and p21 protein expression (FIG. 5a). We also observed an increase in phospho38 and a decrease of phospho-AKT amount (FIG. 6c). To understand the relationship between these pathway and apoptosis, the effect of various pathway inhibitors on the ICN1 induced podocyte apoptosis were studied. SB203580, an inhibitor of the p38 pathway and GSI XX did not alter the increase in annexinV positive cell number (FIG. 5e) (p38 data is not shown). On the contrary, pifithrin alpha an inhibitor of p53 pathway decreased the ICN1 induced podocyte apoptosis, indicating the role of p53.

In summary, these results indicate that ICN1 is a strong apoptosis inducer in podocytes likely via the activation of p53 pathway.

Notch1 is Critical for the TGFβ Induced Podocyte Apoptosis

Notch interaction with other cytokines and signaling mechanisms was investigated in podocytes. TGFβ is one of the most important cytokines playing a role in glomerulosclerosis. In addition interaction between TGFβ and the Notch pathway has been described[26-28].

Figures 7A, 7B, 7C, 7D, 7E:
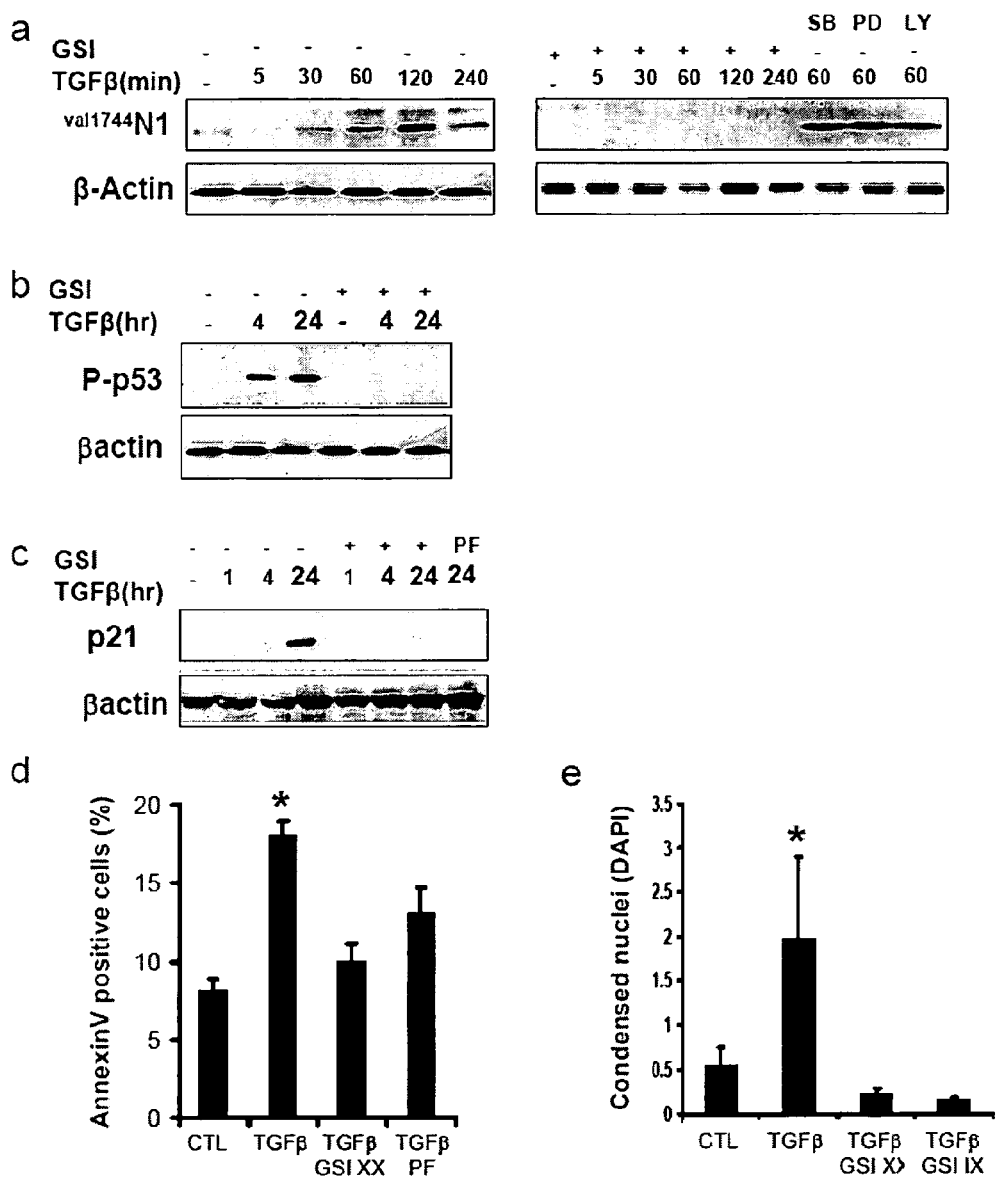
FIG. 7A-7E. Transforming growth factorβ treatment increases active Notch1 levels in podocytes. A, Western blot analysis of ICN1, β-actin, following incubation of the cells with 5 ng/ml TGFβ in the presence or absence of gamma secretase inhibitor (GSI-XX) DBZ (1 µM), 10 µM SB203580, PD or LY. Western blot analysis of p53 (B), and p21 (C) and β-actin levels, following incubation of the cells with 5 ng/ml TGFβ in the presence or absence of GSIXX D. The percent of AnnexinV positive cells, at 24 hrs following TGFβ treatment in the presence or absence of GSIXX (1 µM) or pifitrinα (PF) (15 µM). e. Percent of podocytes with condensed nuclei (apoptotic) 24 hrs after TGFβ treatments in the presence or absence of GSI XX (1 µM) or GSI IX (1 µM) treatment.
Figures 8A, 8B:
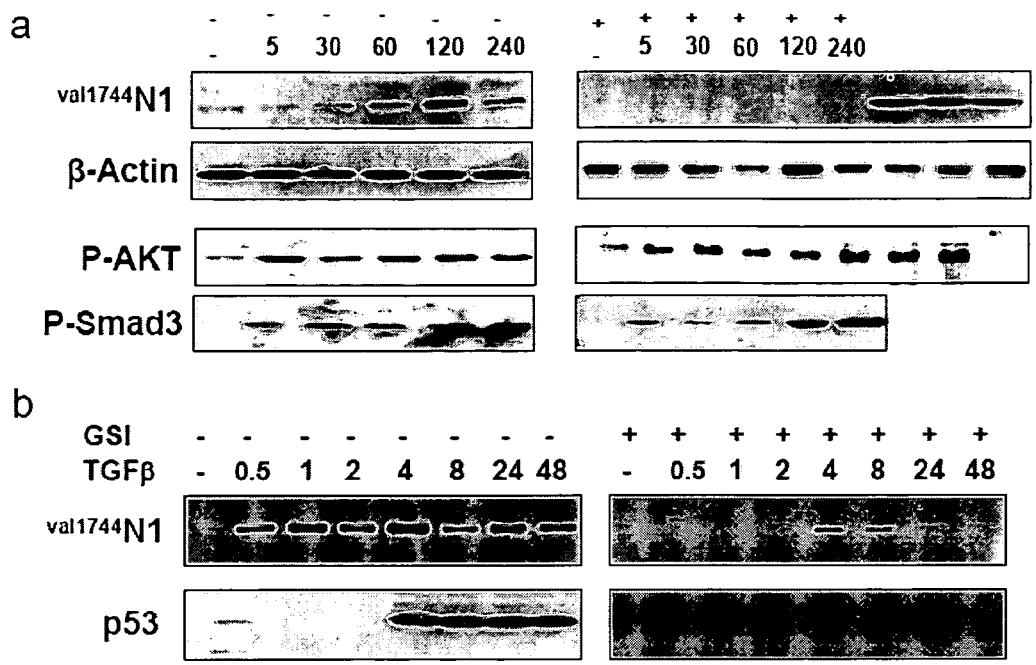
FIG. 8A-8B. Western blot analysis of ICN1, beta action, phospho-p38, phospho-AKT and phospho-Smad3 following 5 ng/ml TGFβ treatment, in the presence or absence of GSI XX (1 µM) or 10 µM SB203580, PD or LY.

TGFβ treatment of cultured podocytes led to an increase of ICN1 levels as early as 30 minutes (FIG. 7a). This increase was fully sensitive to 100 nM gamma secretase inhibitor XX (GSIXX or DBZ) (FIG. 7a) or to GSI IX and GSI X (data not shown), but it was not sensitive p38 (SB203580), AKT (LY294002) or MEK (PD98059) inhibitor treatments (FIG. 7a). Incubation of podocytes in GSI XX did not interfere with the TGFβ induced Smad3 and Akt phosphorylation (FIG. 8a). After 4 hrs of incubation phosphorylated p53 levels were increased and it was fully sensitive to GSIXX (FIG. 7b). TGFβ treatment also led to an increase in p21 protein expression (after 24 hrs), which could be blocked by the GSI inhibitor and by pifithrinα (inhibitor of p53) (FIG. 7c), indicating that p21 is downstream of p53 activation.

To assess whether the TGFβ induced Notch and downstream p53 activation play a roles in the TGFβ induced podocyte apoptosis, counts were made of annexinV positive cell number. Pre-incubation of the cells with GSIXX or pifithrinα prevented TGFβ induced increased in annexinV positive cell number (FIG. 7d). Similar results were obtained when apoptosis was evaluated by nuclear condensation assay (by DAPI) staining (FIG. 7e). Control experiments indicated that GSIXX did not affect ICN1 induced apoptosis (FIG. 5e). In addition downstream p53 target genes; Bax and Apaf1 mRNA levels were increased following TGFβ treatment, and this increase was sensitive to gamma-secretase inhibitor treatment (FIGS. 7f, 7g).

These results indicate that TGFβ led to an (GSI sensitive) increase in active Notch1 levels in cultured podocytes. Increased active Notch levels play a critical role in TGFβ induced podocyte apoptosis likely via interacting with the p53 pathway.

Figures 10A, 10B, 10C, 10D:
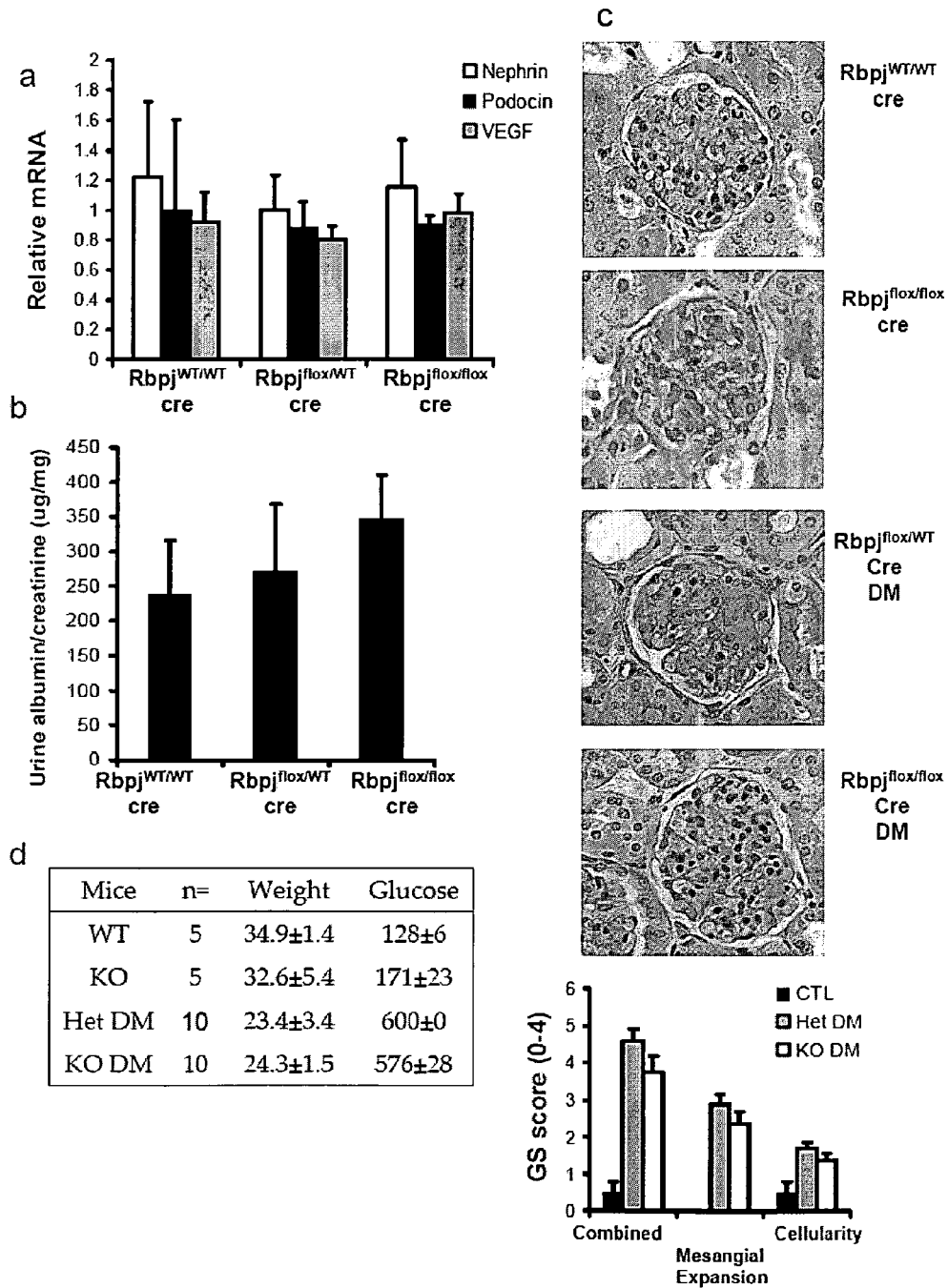
FIG. 10A-10D. Effect of podocyte specific Rbpj deletion on the development of diabetic nephropathy. A. Relative mRNA levels of nephrin, podocin and VEGF in glomerular extracts and B. albuminuria by albumin/creatinine ratio of 20 weeks old male pod$^{cre}$ Rbpj$^{wt/wt}$ pod$^{cre}$ Rbpj$^{flox/wt}$ pod$^{cre}$ Rbpj$^{flox/flox}$ male mice C. PAS staining and the semi-quantitative assessment of PAS staining, D. body weight and serum glucose levels of 20 week old male control (pod$^{cre}$ Rbpj$^{flox/wt}$ pod$^{cre}$ Rbpj$^{flox/flox}$), diabetic wild type (podcre Rbpj$^{flox/wt}$) and knock-out diabetic (KO-DM) podocincreRbpj$^{flox/flox}$ animals.

Podocyte Specific Inactivation of the Rbpj Reduces Kidney Injury in Murine Diabetic Nephropathy Model In order to evaluate the role of the Notch pathway specifically in podocytes in glomerular diseases, mice were generated with podocyte specific deletion of Rbpj, (which is the common transcriptional co-factor of the different Notch isoforms), by intercrossing two existing mouse stains the podocin$^{cre}$ and the Rbpj$^{flox}$ mice[29, 30]. Mice with podocyte specific deletion did not show renal histological abnormalities, albuminuria, or change in important podocyte specific gene expression (FIGS. 10b, 10c). These findings indicate the dispensable role of the Notch/Rbpj pathway in mature glomeruli (after the capillary loop stage).

Figures 9A, 9B, 9C, 9D, 9E:
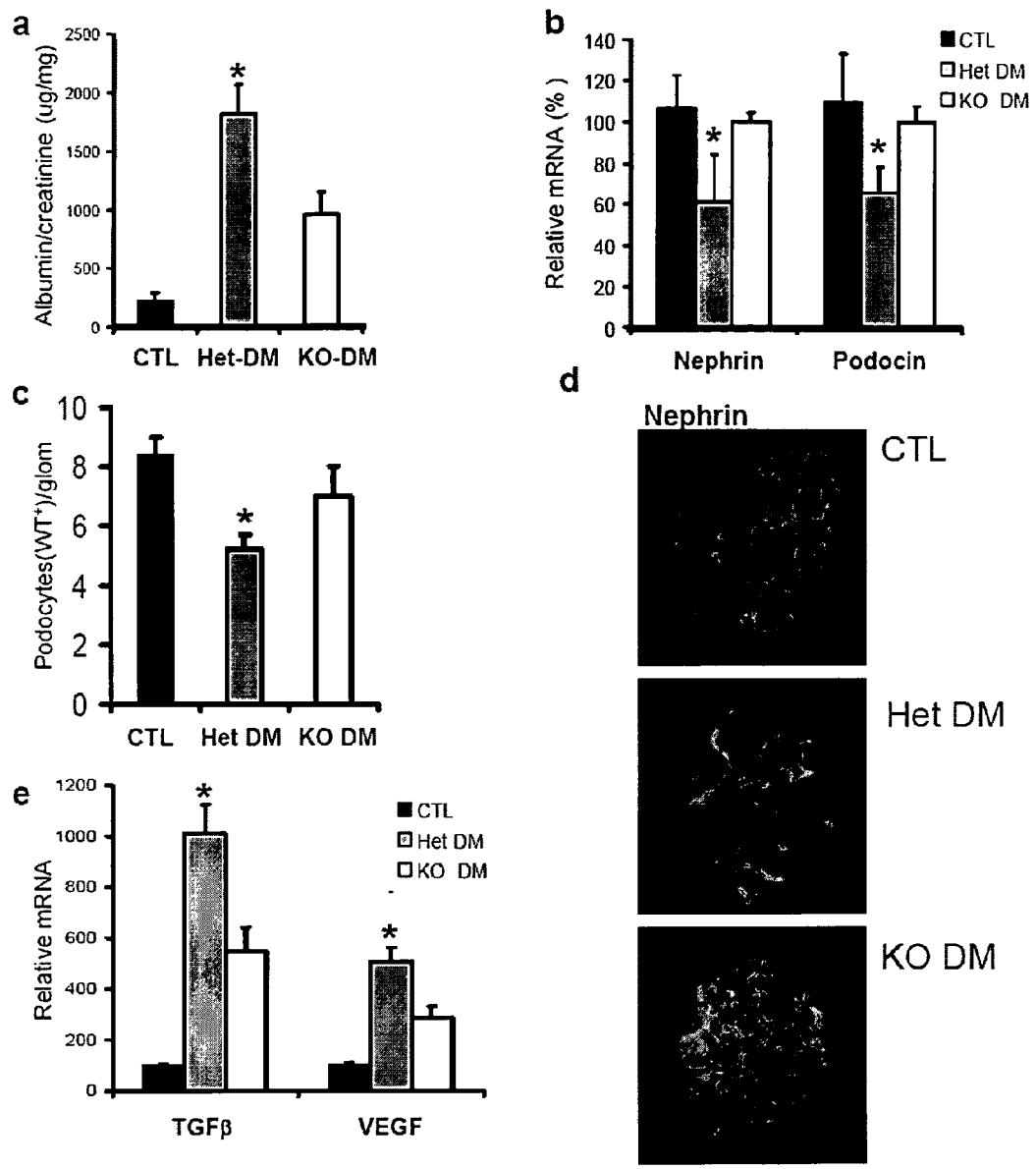
FIG. 9A-9E. Effect of podocyte specific Rbpj deletion on the development of diabetic nephropathy. A. Albuminuria measured as albumin/creatinine ratio µg/mg creatinine of control (CTL) non-diabetic 20 weeks old male (pod$^{cre}$ Rbpj$^{flox/wt}$ pod$^{cre}$ Rbpj$^{flox/flox}$) and diabetic pod$^{cre}$ Rbpj$^{flox/wt}$ (Het-DM) and pod$^{cre}$ Rbpj$^{flox/flox}$ (KO-DM). B. Relative mRNA amount of nephrin, podocin, (E) TGFβ and VEGF by QRT-PCR analysis of whole kidney extracts of 20 week old male (pod$^{cre}$ Rbpj$^{flox/wt}$ pod$^{cre}$ Rbpj$^{flox/flox}$) and diabetic pod$^{cre}$ Rbpj$^{flox/wt}$ (Het-DM) and pod$^{cre}$ Rbpj$^{flox/flox}$ (KO-DM) mice C. WT-1 positive cell number and D. nephrin immunostaining of 20 week old male (pod$^{cre}$ Rbpj$^{flox/wt}$ pod$^{cre}$ Rbpj$^{flox/flox}$) and diabetic pod$^{cre}$ Rbpj$^{flox/wt}$ (Het-DM) and pod$^{cre}$ Rbpj$^{flox/flox}$ (KO-DM) mice. * represents p<0.05

Diabetic nephropathy was induced in uninephrectomized male mice via low dose streptozotocin injection at 5 weeks of age. Male (n=10) podocin$^{cre}$Rbpj$^{flox/flox}$ podocin$^{cre}$Rbpj$^{flox/wt}$ littermates were used for the comparison. Wild type animals developed significant albuminuria by 20 weeks of age. Albuminuria was about 50% lower in diabetic podocin$^{cre}$Rbpj$^{flox/flox}$ mice, compared to podocin$^{cre}$Rbpj$^{flox/wt}$ mice (960 μg/mg vs. 1830 μg/mg albumine/creatinine, respectively) (FIG. 9a), despite the similar degree of hyperglycemia (FIG. 10d). Podocyte specific genes; nephrin and podocin showed a significant (40%) reduction in control diabetic mice; this reduction was absent in diabetic Rbpj deleted animals (FIGS. 9b, 9d). This change correlated with an about 40% reduction in wild type (WT) positive podocyte number in podocin$^{cre}$Rbpj$^{flox/wt}$ diabetic animals, while there was no statistical difference between control and diabetic podocin$^{cre}$Rbpj$^{flox/flox}$ mice (FIG. 9c). Diabetic animals also showed an increase of mRNA levels of TGFβ and VEGF, which was abrogated in diabetic podocyte specific Rbpjdeleted mice (FIG. 9e). The mesangial expansion observed in control diabetic animals, was somewhat lower in mice with Rbpj deletion; however, the difference was not statistically significant (FIG. 10c).

In summary, in vivo podocyte specific deletion of the Notch/Rbpj pathway with the use of the podocin$^{cre}$Rbpj$^{flox/flox}$ mice reduces diabetic kidney injury and it demonstrates that the Notch pathway reactivation in diabetic podocytes plays a critical role in the development diabetic albuminuria and podocyte loss.

Figures 11A, 11B, 11C, 11D, 11E, 11F:
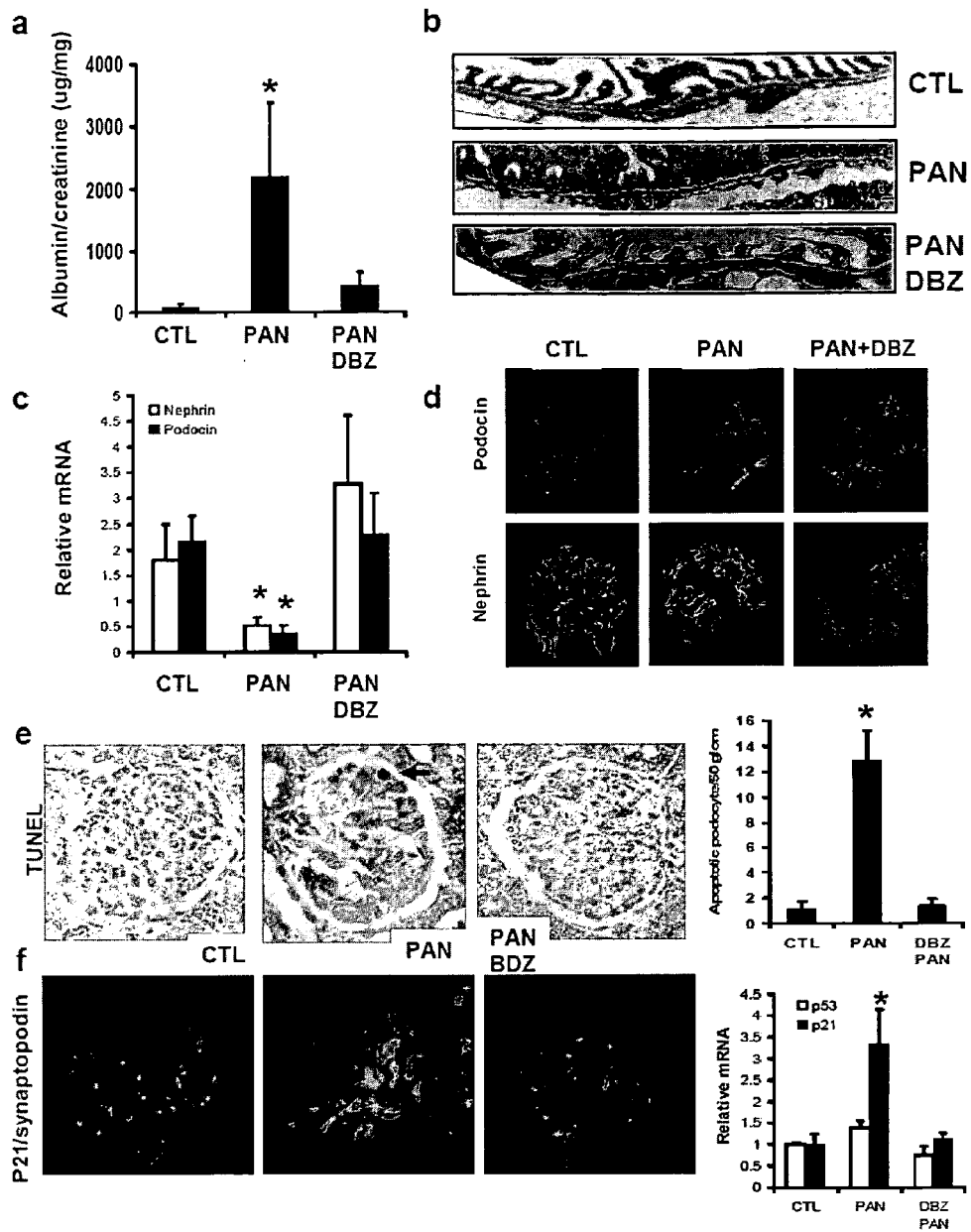
FIG. 11A-11F. Gamma secretase treatment ameliorates glomerular disease in PAN induced nephrotic syndrome. A. Albumin/creatinine ratio of control and after 6 days of PAN or PAN+DBZ administration. N=8 control and PAN and n=5 of PAN+DBZ treated rats B. Transmission electron microscopy of control, PAN and PAN+DBZ treated rats. C. QRT-PCR analysis of nephrin and podocin gene expression of isolated glomerular samples control PAN and PAN+DBZ treated rats (on day 8). D. Immunostaining with nephrin and podocin of control PAN and PAN+DBZ treated rats. E. Representative images and quantification of TUNEL staining of control and treated rats. (The arrow indicates positive nuclear staining in glomerular epithelial cells.) F. QRT-PCR analysis of p53 and p21 mRNA amounts of whole kidney lysates of control, PAN and BDZ+PAN treated rats. * denotes significance p<0.05.
Figures 12A, 12B, 12C:
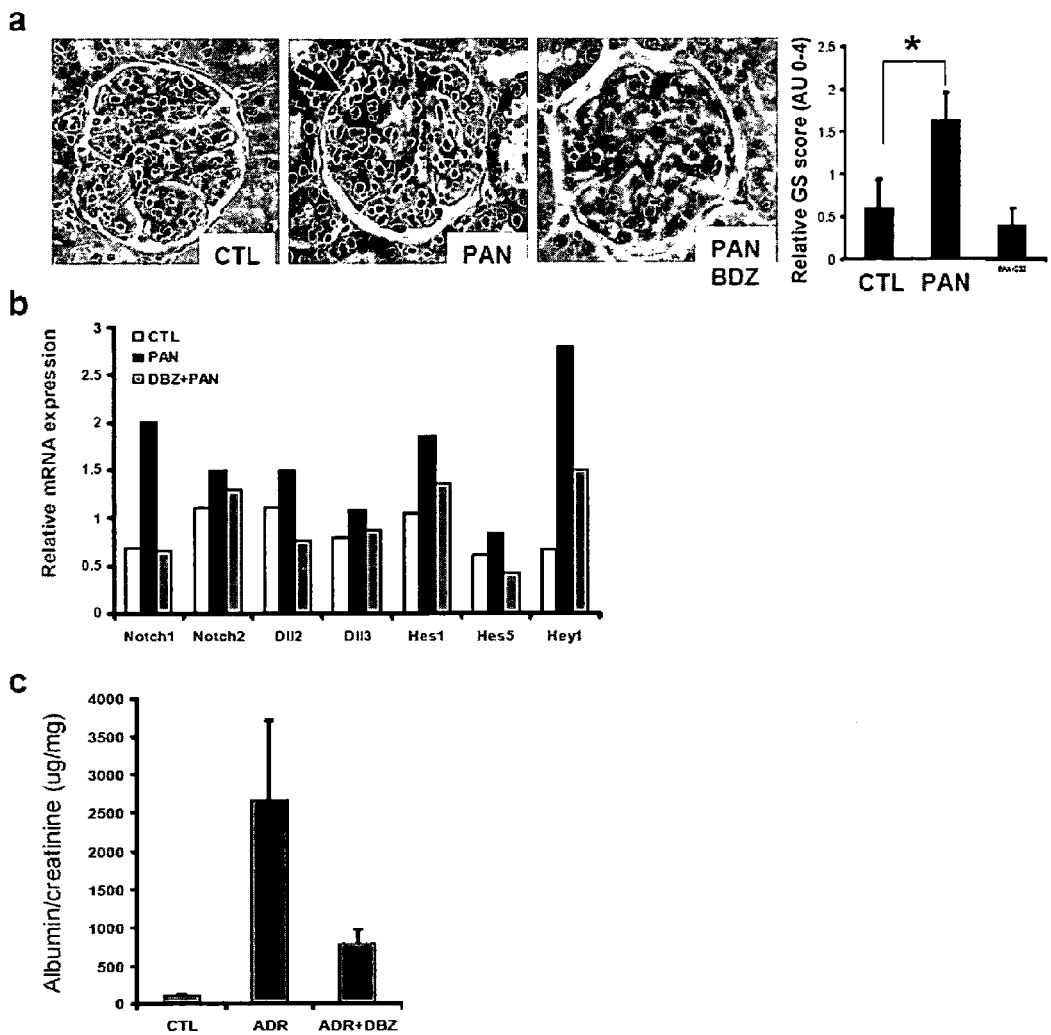
FIG. 12A-12C. A. Renal histology of PAS stained kidney sections of control PAN and PAN+DBZ treated rats. The arrow indicates increased segmental sclerosis of PAN rats. Semi-quantitative analysis of the glomerular histology of control, PAN and PAN+DBZ treated rats on scale (0-4). B. QRT-PCR analysis of (whole kidney extracts) of Notch pathway gene expression of control, PAN and PAN+DBZ treated rats. C. Albuminuria by urine albumin/creatinine ratio (μg/mg creatinine) of 8 weeks old male control (CTL) 12 mg/kg adriamycin treated (ADR) and DBZ+adriamycin treated mice (12 days following ADR and DBZ administration).

Gamma Secretase Treatment Ameliorates Proteinuria in Rat Model of Glomerular Disease It was examined whether the Notch pathway inhibition (with the use of a gamma-secretase inhibitor) could be used as a potential strategy for the treatment of albuminuric glomerular disease[31]. Rats we treated with DBZ 500 μg/100 gr ip. daily stating 12 hrs prior to PAN injection. Animals were sacrificed on day 8 as the PAN treated rats appeared moribund and most of them had severe nephrotic syndrome (ascites and edema). DBZ treatment normalized the Notch pathway gene expression increase of PAN treated rats (FIG. 1e, FIG. 12a). Animals treated with BDZ and PAN had significantly less albuminuria compared to animals treated with PAN only (FIG. 11a). Similarly EM analysis showed severe foot process effacement in PAN treated rats, which was almost fully abrogated in rats that were treated with DBZ also (FIG. 11b). In conjunction DBZ treatment also protected rats from a decrease in nephrin and podocin levels both at the mRNA and protein levels (FIGS. 11c, 11d). Renal histology showed mild but significant glomerulosclerosis in the PAN treated rats, which was absent in rats pretreated with the γ-secretase inhibitor (FIG. 12b). Podocyte apoptosis (examined by TUNEL staining), which was observed following PAN treatment, was fully prevented by DBZ treatment (FIG. 11e). Similarly, expression of p53 and p21 was lower in BDZ treated rats compared to PAN only injected animals (FIG. 11O.

Similar results were obtained in the doxorubicin induced nephrotic syndrome of mice. 12 days following doxorubicin treatment male Balb/c mice had significant albuminuria at 2659 μg/mg creatinine, while treatment of mice with DBZ significantly lowered albuminuria to 800 μg/mg creatinine (FIG. 12c).

In summary the gamma-secretase inhibitor, DBZ ameliorated albuminuria in mouse and rat models of nephrotic syndrome, likely via inhibiting Notch activation and protecting from podocyte apoptosis.

Discussion

These experiments provide evidence for the role of the Notch pathway in the development of glomerular disease. The role of Notch in tubular disease is provided in the following Example. Notch is an evolutionarily conserved local cell signaling mechanism that participates in a variety of cellular processes[14-16]. Following organ development Notch can be both tumor suppressive or oncogenic[25, 31, 32], it can help to maintain stem cell population in the brain and it can induce damage following ischemic injury[33, 34]. Little is known about this signaling pathway in the adult kidney. The present results show that this pathway is reactivated (mainly in podocytes) in various glomerular diseases. The peak of the activation coincided with the height of the podocyte apoptosis; at 8 weeks of age in diabetic Lepr$^{db/db}$ kidneys[9], 6-8 days following PAN injection[35]. The present series of in vitro and in vivo studies confirmed the causal association between Notch and apoptosis in podocytes. Notch activation may represent a maladaptive attempt for renal regeneration. During development, Notch expression correlates with a burst of cell proliferation and suppression of Pax-2. In mature podocytes, proliferation was not an apparent phenotype either after ICN1 overexpression, or in human and experimental models of DNP and FSGS. Alternatively re-activation of Notch could be associated with a less differentiated cellular phenotype and programming the cells for regeneration. However, in the present experiments, inactivation of Notch protected from glomerular damage and activation of the pathway led to severe podocyte damage. This might be related to mature podocytes exiting the cell cycle and suppressing the expression of some other genes that could help them to regenerate; thereby increased Notch activity led to activation of the a programmed cell death pathway leading to podocyte depletion, albuminuria glomerulosclerosis and eventually end stage kidney disease. This cellular response (after Notch activation) of the podocytes seems to resemble other terminally differentiated epithelial cells (keratinocytes and neurons). In neurons and in keratinocytes Notch leads to p53 and p21 activation leading to cell cycle arrest and apoptosis[27, 36-38]. A similar mechanism is proposed in podocytes. It is also interesting to note that ICN1 overexpression in tubular epithelial cells (cells that are known for their proliferative and regenerative capacity) does not induce apoptosis (unpublished observation). These observations confirm and emphasize the time and cell type specific role of Notch.

Notch interacts with the TGFβ pathway to mediate podocyte damage in diabetes and focal segmental glomerulosclerosis[36]. The present studies indicate that TGFβ can elevate active Notch levels in podocytes. There are multiple possibilities how this may happen: TGFβ treatment of podocytes leads to an increase of Jagged 1 mRNA, a direct interaction between Smad3 and ICN has been described, and several Hey and Hes genes are direct targets of TGFβ[28]. Further studies are needed to differentiate between these possibilities in podocytes. The present experiments also indicate that TGFβ not only leads to an increase in active ICN1 levels, but Notch1 over-expression was also associated with increases of TGFβ level (in vivo and in vitro models). Thereby a positive feed-back loop appears to exist between the TGFβ and the Notch pathway. In this signaling network the Notch pathway activation appears to play a crucial role in the regulation of podocyte apoptosis. Inhibition of the Notch pathway blocks TGFβ induced apoptosis.

The present studies indicate that manipulation of specific signaling pathways only in podocytes can ameliorate the development of DNP. It is well known in humans and in animal models of glomerular disease that podocyte density correlates the best with albuminuria[8]. The present data provide experimental evidence for the role of podocytes mediating the development of albuminuria in DNP. Diabetic podocincre RBPJ$^{flox/flox}$ mice have about 50% reduction in albuminuria compared to podocin$^{cre}$ RBPJ$^{flox/wt}$ animals. This degree of reduction in albuminuria might be expected based on the fact that the cre mediated Rbpj excision is unlikely to be 100%. In addition contribution of other parallel pathways can not be excluded based on the present results. The present results also indicate that the development of mesangial expansion might occur parallel to the podocyte dysfunction and multiple cell types are affected simultaneously.

The present data indicate that gamma-secretase inhibitors are of therapeutic benefit in glomerular disease. Large number of these inhibitors have been developed and tested over the last decade. They appear to have a therapeutic benefit in animal models for Alzheimer's disease, acute lymphoblastic leukemia of childhood (which is associated with a mutation of Notch), colon cancer, and ischemic stroke[31, 39]. A Notch inhibitor is in Phase I clinical trials for patients with breast cancer tumors (ClinicalTrials.gov Identifier NCT00106145).

Example II

Tubulointerstitial Fibrosis

The Notch pathway is important in the development of podocytes and proximal tubules. As opposed to the glomerular podocytes, proximal tubular epithelial cells fully regenerate after toxic/ischemic renal damage. Although the exact mechanism of tubular regeneration is not fully clear, one suggested mechanism could include re-activation of the developmental pathway including Notch and wnt. The present Example indicates that the Notch signaling plays a role in the regeneration phase after tubular injury when other developmental genes are known to be re-activated (Pax-2, Wnt4).

Sparse expression of active Notch1 and 2 was observed in the tubules of normal healthy adult rodent and human kidneys, consistent with the notion that these are renal progenitor cells. Experiments were conducted using the murine folic acid (FA)-induced nephrotoxicity model, which is characterized by acute tubular injury followed by both tubular regeneration and chronic changes such as patchy interstitial fibrosis. Strong upregulation was found for mRNA levels of Notch 1-4, the ligands Jagged 1 and 2, delta like-1 and -4, and the downstream target genes Hes1, Hey1, and HeyL in total kidney homogenates 1 day after FA injection, which remained increased up to 1 week. Immunostainings for Notch 1 intracellular domain showed a strong nuclear expression in tubular cells of FA-treated mice after 1 day, confirming activation of Notch signaling.

Increased Notch pathway gene expression was also observed in mouse models of chronic tubulointerstitial fibrosis (unilateral ureteral obstruction) and in patients with chronic renal disease and tubulointerstitial fibrosis. Active Notch1 and 2 expression were markedly increased in injured tubules and were also present in tubulointerstitial cells.

To further investigate the role of Notch in FA-induced renal injury, mice were treated for 1 week with the gamma-secretase inhibitor (GSI) dibenzazepine (DBZ) that blocks activation of the Notch pathway by interfering with Notch cleavage. Pretreatment of animals with GSI prior to the toxic damage did not change tubular apoptosis rate and tubular damage score. In control kidneys, large numbers of interstitial fibroblasts and significant tubulointerstitial fibrosis were observed indicating a misdirected renal regeneration. However, tubulointerstitial fibrosis (observed on histology) and profibrotic gene expression (collagen, fibronectin etc.) was significantly reduced in animals treated with GSI, indicating that Notch activation was directing the cells into a more mesenchymal (less differentiated) cell fate. DBZ treatment completely blunted the rise in HeyL expression but did not affect the increase in serum creatinine, tubular damage scores or the rate of tubular apoptosis evaluated by interstitial cell aggregates that mark an early stage of developing fibrosis. FA-induced upregulation of genes that are known to be involved in fibrotic remodeling such as TGF-β, fibronectin, MMP-2 and 9 was greatly reduced in the DBZ treated group of mice.

The role and regulation of Notch pathway genes were also examined in other models of tubulointerstitial fibrosis. Notch pathway genes were upregulated in the unilateral ureteral obstruction model of renal tubulointerstitial fibrosis. To examine the role of Notch activation in this model, animals were injected with GSI XX (DBZ). DBZ reduced the expression of Notch target gene HeyL and reduced expression of pro-fibrotic genes collagen, fibronectin and alpha smooth muscle action. DBZ also reduced tubulointerstitial fibrosis (evaluated on PAS staining).

In additional experiments, cultured renal tubular epithelial cells were used to further understand the mechanism of Notch activation in the renal tubules during injury and regeneration. In vitro transforming growth factorβ treatment caused activation of Notch1 in cultured tubular epithelial cells via the regulation of its ligand Jagged1 inducing epithelial to mesenchymal transition, which was dependent on Jagged 1 and Notch activation. In further experiments, active Notch1 and Notch2 were overexpressed in rat tubular epithelial cells. No increase of apoptosis was observed following tubular expression of Notch1 and 2, but there was increased expression of mesenchymal gene alpha smooth muscle actin. Notch was found to mediate proliferation of tubular epithelial cells most likely via activation of cyclinD1 and beta catenin.

In summary, increased Notch1 activity was observed in acute and chronic renal tubular injury models. GSI treatment did not compromise renal regeneration following injury, but prevented tubulointerstitial fibrosis indicating that Notch might be directing cells into more mesenchymal faith under these circumstances. The results indicate that Notch plays an important role in the early stages of tubulointerstitial fibrosis (TIF). Limiting TIF with gamma-secretase inhibitors is thus expected to have therapeutic benefit in kidney disease.

REFERENCES

1. State-specific trends in chronic kidney failure—United States, 1990-2001. MMWR Morb Mortal Wkly Rep 53, 918-20 (2004).
2. Somlo, S. & Mundel, P. Getting a foothold in nephrotic syndrome. Nat Genet 24, 333-5 (2000).
3. Boute, N. et al. NPHS2, encoding the glomerular protein podocin, is mutated in autosomal recessive steroid-resistant nephrotic syndrome. Nat Genet 24, 349-54 (2000).
4. Kaplan, J. M. et al. Mutations in ACTN4, encoding alpha-actinin-4, cause familial focal segmental glomerulosclerosis. Nat Genet 24, 251-6 (2000).
5. Reiser, J. et al. TRPC6 is a glomerular slit diaphragm-associated channel required for normal renal function. Nat Genet 37, 739-44 (2005).
6. Winn, M. P. et al. A mutation in the TRPC6 cation channel causes familial focal segmental glomerulosclerosis. Science 308, 1801-4 (2005).
7. Wolf, G., Chen, S. & Ziyadeh, F. N. From the periphery of the glomerular capillary wall toward the center of disease: podocyte injury comes of age in diabetic nephropathy. Diabetes 54, 1626-34 (2005).
8. Pagtalunan, M. E. et al. Podocyte loss and progressive glomerular injury in type II diabetes. J Clin Invest 99, 342-8 (1997).
9. Susztak, K., Raff, A. C., Schiffer, M. & Bottinger, E. P. Glucose-induced reactive oxygen species cause apoptosis of podocytes and podocyte depletion at the onset of diabetic nephropathy. Diabetes 55, 225-33 (2006).
10. Yu, D. et al. Urinary podocyte loss is a more specific marker of ongoing glomerular damage than proteinuria. J Am Soc Nephrol 16, 1733-41 (2005).
11. Jarriault, S. et al. Signalling downstream of activated mammalian Notch. Nature 377, 355-8 (1995).
12. Schweisguth, F. Notch signaling activity. Curr Biol 14, R129-38 (2004).
13. Ilagan, M. X. & Kopan, R. SnapShot: notch signaling pathway. Cell 128, 1246 (2007).
14. Cheng, H. T. et al. Notch2, but not Notch1, is required for proximal fate acquisition in the mammalian nephron. Development 134, 801-11 (2007).
15. Cheng, H. T. & Kopan, R. The role of Notch signaling in specification of podocyte and proximal tubules within the developing mouse kidney. Kidney Int 68, 1951-2 (2005).
16. Wang, P., Pereira, F. A., Beasley, D. & Zheng, H. Presenilins are required for the formation of comma- and S-shaped bodies during nephrogenesis. Development 130, 5019-29 (2003).
17. McCright, B. Notch signaling in kidney development. Curr Opin Nephrol Hypertens 12, 5-10 (2003).
18. Vooijs, M. et al. Mapping the consequence of Notch1 proteolysis in vivo with NIP-CRE. Development 134, 535-44 (2007).
19. Liu, Y., Pathak, N., Kramer-Zucker, A. & Drummond, I. A. Notch signaling controls the differentiation of transporting epithelia and multiciliated cells in the zebrafish pronephros. Development 134, 1111-22 (2007).
20. Drummond, K. & Mauer, M. The early natural history of nephropathy in type 1 diabetes: II. Early renal structural changes in type 1 diabetes. Diabetes 51, 1580-7 (2002).
21. Chen, L. & Al-Awqati, Q. Segmental expression of Notch and Hairy genes in nephrogenesis. Am J Physiol Renal Physiol 288, F939-52 (2005).
22. Piscione, T. D., Wu, M. Y. & Quaggin, S. E. Expression of Hairy/Enhancer of Split genes, Hes1 and Hes5, during murine nephron morphogenesis. Gene Expr Patterns 4, 707-11 (2004).
23. Shigehara, T. et al. Inducible podocyte-specific gene expression in transgenic mice. J Am Soc Nephrol 14, 1998-2003 (2003).
24. Stanger, B. Z., Datar, R., Murtaugh, L. C. & Melton, D. A. Direct regulation of intestinal fate by Notch. Proc Natl Acad Sci USA 102, 12443-8 (2005).
25. Zweidler-McKay, P. A. et al. Notch signaling is a potent inducer of growth arrest and apoptosis in a wide range of B cell malignancies. Blood (2005).
26. Zavadil, J., Cermak, L., Soto-Nieves, N. & Bottinger, E. P. Integration of TGF-beta/Smad and Jagged1/Notch signalling in epithelial-to-mesenchymal transition. Embo J 23, 1155-65 (2004).
27. Niimi, H., Pardali, K., Vanlandewijck, M., Heldin, C. H. & Moustakas, A. Notch signaling is necessary for epithelial growth arrest by TGF-beta. J Cell Biol 176, 695-707 (2007).
28. Blokzijl, A. et al. Cross-talk between the Notch and TGF-beta signaling pathways mediated by interaction of the Notch intracellular domain with Smad3. J Cell Biol 163, 723-8 (2003).
29. Oka, C. et al. Disruption of the mouse RBP-J kappa gene results in early embryonic death. Development 121, 3291-301 (1995).
30. Moeller, M. J., Sanden, S. K., Soofi, A., Wiggins, R. C. & Holzman, L. B. Podocyte-specific expression of cre recombinase in transgenic mice. Genesis 35, 39-42 (2003).
31. van Es, J. H. et al. Notch/gamma-secretase inhibition turns proliferative cells in intestinal crypts and adenomas into goblet cells. Nature 435, 959-63 (2005).
32. Ciofani, M. & Zuniga-Pflucker, J. C. Notch promotes survival of pre-T cells at the beta-selection checkpoint by regulating cellular metabolism. Nat Immunol 6, 881-8 (2005).
33. Arumugam, T. V. et al. Gamma secretase-mediated Notch signaling worsens brain damage and functional outcome in ischemic stroke. Nat Med 12, 621-3 (2006).
34. Akai, J., Halley, P. A. & Storey, K. G. FGF-dependent Notch signaling maintains the spinal cord stem zone. Genes Dev 19, 2877-87 (2005).
35. Kim, Y. H. et al. Podocyte depletion and glomerulosclerosis have a direct relationship in the PAN-treated rat. Kidney Int 60, 957-68 (2001).
36. Zavadil, J. et al. Genetic programs of epithelial cell plasticity directed by transforming growth factor-beta. Proc Natl Acad Sci USA 98, 6686-91 (2001).
37. Rangarajan, A. et al. Notch signaling is a direct determinant of keratinocyte growth arrest and entry into differentiation. Embo J 20, 3427-36 (2001).
38. Nicolas, M. et al. Notch1 functions as a tumor suppressor in mouse skin. Nat Genet 33, 416-21 (2003).
39. Wolfe, M. S. Therapeutic strategies for Alzheimer's disease. Nat Rev Drug Discov 1, 859-66 (2002).

40. Kato, H. et al. Involvement of RBP-J in biological functions of mouse Notch1 and its derivatives. Development 124, 4133-41 (1997).
41. Mundel, P. et al. Synaptopodin: an actin-associated protein in telencephalic dendrites and renal podocytes. J Cell Biol 139, 193-204 (1997).
42. U.S. Pat. No. 6,756,511, issued Jun. 29, 2004, Gamma-secretase inhibitors, Castro Pineiro et al.
43. U.S. Pat. No. 6,890,956, issued May 10, 2005, Cyclohexyl sulphones as gamma-secretase inhibitors, Churcher et al.
44. U.S. Pat. No. 6,984,626, issued Jan. 10, 2006, Gamma-secretase inhibitors, Nadin et al.
45. U.S. Pat. No. 7,049,296, issued May 23, 2006, Gamma-secretase inhibitors, Castro Pineiro et al.
46. U.S. Pat. No. 7,101,895, issued Sep. 5, 2006, Cyclohexyl sulphone derivatives as gamma-secretase inhibitors, Churcher et al.
47. U.S. Pat. No. 7,138,400, issued Nov. 21, 2006, Sulfamides as gamma-secretase inhibitors, Collins et al.
48. U.S. Pat. No. 7,144,910, issued Dec. 6, 2006, Sulfonamides, sulfamates and sulfamides as gamma-secretase inhibitors, Madin et al.
49. U.S. Pat. No. 7,183,303, issued Feb. 27, 2007, Gamma-secretase inhibitors, Castro Pineiro et al.
50. Bihel F, Das C, Bowman M J, Wolfe M S. Discovery of a Subnanomolar helical D-tridecapeptide inhibitor of gamma-secretase. J Med Chem. 2004; 47(16):3931-3.
51. Best J D, Smith D W, Reilly M A, O'Donnell R, Lewis H D, Ellis S, Wilkie N, Rosahl T W, Laroque P A, Boussiquet-Leroux C, Churcher I, Atack J R, Harrison T, Shearman M S. The novel gamma secretase inhibitor N-[cis-4-[(4-chlorophenyl)sulfonyl]-4-(2,5-difluorophenyl)cyclohexyl]-1,1,1-trifluoromethanesulfonamide (MRK-560) reduces amyloid plaque deposition without evidence of notch-related pathology in the Tg2576 mouse. J Pharmacol Exp Ther. 2007 February; 320(2):552-8. Epub 2006 Nov. 10.
52. Davies A J, Scott J P, Bishop B C, Brands K M, Brewer S E, Dasilva J O, Dormer P G, Dolling U H, Gibb A D, Hammond D C, Lieberman D R, Palucki M, Payack J F. A novel crystallization-induced diastereomeric transformation based on a reversible carbon-sulfur bond formation. Application to the synthesis of a gamma-secretase inhibitor. J Org Chem. 2007 Jun. 22; 72(13):4864-71. Epub 2007 May 24.
53. El-Gendy A M, Adejare A. Membrane permeability related physicochemical properties of a novel gamma-secretase inhibitor. Int J Pharm. 2004; 280(1-2):47-55.
54. Laras Y, Quéléver G, Garino C, Pietrancosta N, Sheha M, Bihel F, Wolfe M S, Kraus J L. Substituted thiazolamide coupled to a redox delivery system: a new gamma-secretase inhibitor with enhanced pharmacokinetic profile. Org Biomol Chem. 2005 Feb. 21; 3(4):612-8. Epub 2005 Jan. 10.
55. McLendon C, Xin T, Ziani-Cherif C, Murphy M P, Findlay K A, Lewis P A, Pinnix I, Sambamurti K, Wang R, Fauq A, Golde T E. Cell-free assays for gamma-secretase activity. FASEB J. 2000; 14(15):2383-6.
56. Prasad C V, Zheng M, Vig S, Bergstrom C, Smith D W, Gao Q, Yeola S, Polson C T, Corsa J A, Guss V L, Loo A, Wang J, Sleczka B G, Dangler C, Robertson B J, Hendrick J P, Roberts S B, Barten D M. Discovery of (S)-2-((S)-2-(3,5-difluorophenyl)-2-hydroxyacetamido)-N-((S,Z)-3-methyl-4-oxo-4,5-dihydro-3H-benzo[d][1,2]diazepin-5-yl)propanamide (BMS-433796): a gamma-secretase inhibitor with Abeta lowering activity in a transgenic mouse model of Alzheimer's disease. Bioorg Med Chem Lett. 2007 Jul. 15; 17(14):4006-11. Epub 2007 Apr. 30.
57. Shearman M S, Beher D, Clarke E E, Lewis H D, Harrison T, Hunt P, Nadin A, Smith A L, Stevenson G, Castro J L. L-685,458, an aspartyl protease transition state mimic, is a potent inhibitor of amyloid beta-protein precursor gamma-secretase activity. Biochemistry. 2000; 39(30):8698-704.
58. Tomita T, Iwatsubo T. The inhibition of gamma-secretase as a therapeutic approach to Alzheimer's disease. Drug News Perspect. 2004 June; 17(5):321-5.
59. Laura B. Rosen, Julie A. Stone, Andrew Plump, Jinyu Yuan, Tim Harrison, Mary Flynn, Aimee Dallob, Catherine Matthews, Donna Stevenson, Dennis Schmidt, Theresa Palmieri, Mark Leibowitz, Stanford Jhee, Larry Ereshefsky, Ronald Salomon, Greg Winchell, Mark S. Shearman, M. Gail Murphy, Keith M. Gottesdiener. The gamma secretase inhibitor MK-0752 acutely and significantly reduces CSF Abeta40 concentrations in humans. Alzheimer's & Dementia, Volume 2, Issue 3, Page S79 (July 2006).
60. Siemers E, Skinner M, Dean R A, Gonzales C, Satterwhite J, Farlow M, Ness D, May P C. Safety, tolerability, and changes in amyloid beta concentrations after administration of a gamma-secretase inhibitor in volunteers. Clin Neuropharmacol. 2005 May-June; 28(3):126-32.
61. Gamma-Secretase Inhibitor May Have Potential as Disease-Modifying Drug in Alzheimer's Disease. Medscape Medical News 2007. J. K. Beals reporting on press briefing by Dr. Siemers at Alzheimer's Association International Conference on Prevention of Dementia: Abstract HT-005. Presented Jun. 11, 2007.

What is claimed is:
1. A method of treating renal disease in a subject, the method comprising administering to the subject a gamma secretase inhibitor in an amount effective to treat the renal disease, wherein the gamma secretase inhibitor is selected from the group consisting of one of more of:
Z-Leu-Leu-Norleucine-CHO, N-Benzyloxycarbonyl-Leu-leucinal, N-(2-Naphthoyl)-Val-phenylalaninal, N-Benzyloxycarbonyl-Leu-phenylalaninal, 1-(S)-endo-N-(1,3,3)-Trimethylbicyclo[2.2.1]hept-2-yl)-4-fluorophenyl Sulfonamide, Menthyloxycarbonyl-LL-CHO, N-[N-(3,5-Difluorophenacetyl-L-alanyl)]-S-phenylglycine t-Butyl Ester, {1S-Benzyl-4R-[1-(1S-carbamoyl-2-phenethylcarbamoyl)-1S-3-methylbutylcarbamoyl]-2R-hydroxy-5-phenylpentyl}carbamic Acid tert-butyl Ester, 7-Amino-4-chloro-3-methoxyisocoumarin, Z-lle-Leu-CHO, Z-Tyr-lle-Leu-CHO, Z-Cys(t-Bu)-lle-Leu-CHO, N-[N-3,5-Difluorophenacetyl]-L-alanyl-S-phenylglycine Methyl Ester, (2S,3R)-3-(3,4-Difluorophenyl)-2-(4-fluorophenyl)-4-hydroxy-N-((3S)-2-oxo-5-phenyl-2,3-dihydro-1H-benzo[e][1,4]diazepin-3-yl)-butyramide, (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide, N-trans-3,5-Dimethoxycinnamoyl-lle-leucinal, N-tert-Butyloxycarbonyl-Gly-Val-Valinal, Isovaleryl-V-V-Sta-A-Sta-OCH$_3$,

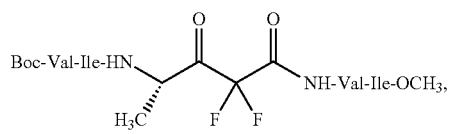

-continued

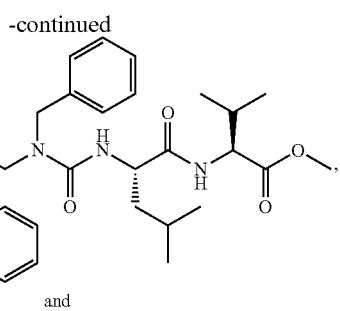

and

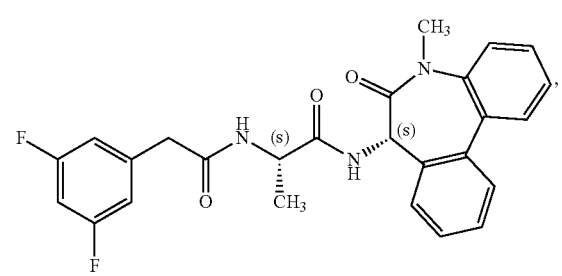

and wherein the renal disease is a glomerular renal disease or a tubular renal disease.

2. The method of claim 1, wherein the subject has diabetes.

3. The method of claim 1, wherein the renal disease is an acute renal disease.

4. The method of claim 1, wherein the renal disease is a chronic renal disease.

5. The method of claim 1, wherein the renal disease is a progressive renal disease.

6. The method of claim 1, wherein the renal disease is a glomerular renal disease.

7. The method of claim 6, wherein the renal disease is diabetic nephropathy.

8. The method of claim 1, wherein the renal disease is tubular renal disease.

9. The method of claim 1, wherein the gamma secretase inhibitor is selected from the group consisting of one of more of:

N-[N-(3,5-Difluorophenacetyl-L-alanyl)]-S-phenylglycine t-Butyl Ester;

{1S-Benzyl-4R-[1-(1S-carbamoyl-2-phenethylcarbamoyl)-1S-3-methylbutylcarbamoyl]-2R-hydroxy-5-phenylpentyl}carbamic Acid tert-butyl Ester; and

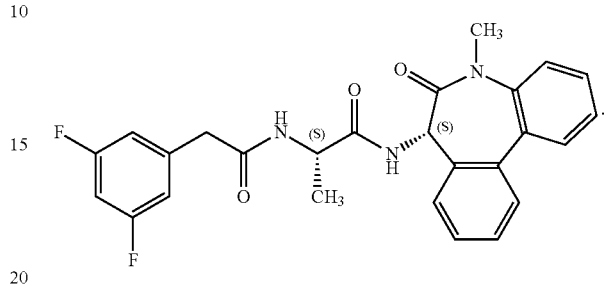

10. The method of claim 9, wherein the gamma secretase inhibitor is

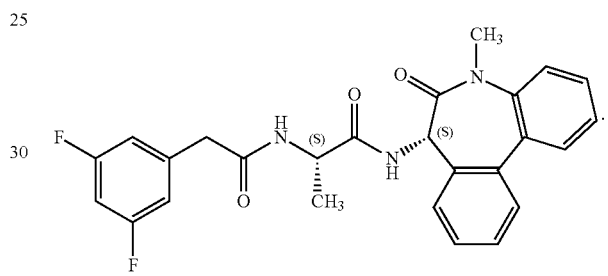

* * * * *